(12) United States Patent
Schramm et al.

(10) Patent No.: US 8,835,467 B2
(45) Date of Patent: Sep. 16, 2014

(54) SIR2 REGULATION

(71) Applicants: Vern L. Schramm, New Rochelle, NY (US); Anthony A. Sauve, Bronx, NY (US)

(72) Inventors: Vern L. Schramm, New Rochelle, NY (US); Anthony A. Sauve, Bronx, NY (US)

(73) Assignee: Albert Einstein College of Medicine of Yeshiva University, Bronx, NY (US)

( * ) Notice: Subject to any disclaimer, the term of this patent is extended or adjusted under 35 U.S.C. 154(b) by 0 days.

(21) Appl. No.: 13/747,543

(22) Filed: Jan. 23, 2013

(65) Prior Publication Data

US 2013/0231351 A1 Sep. 5, 2013

Related U.S. Application Data

(63) Continuation of application No. 10/560,676, filed as application No. PCT/US2004/020902 on Jun. 30, 2004, now Pat. No. 8,383,653.

(60) Provisional application No. 60/484,321, filed on Jul. 2, 2003.

(51) Int. Cl.
| | | |
|---|---|---|
| *A61K 31/445* | (2006.01) | |
| *C12Q 1/34* | (2006.01) | |
| *C07D 241/24* | (2006.01) | |
| *C07D 213/83* | (2006.01) | |
| *A61K 38/00* | (2006.01) | |
| *A61K 31/4965* | (2006.01) | |
| *A61K 31/455* | (2006.01) | |
| *A61K 31/166* | (2006.01) | |
| *C07D 213/81* | (2006.01) | |

(52) U.S. Cl.
CPC .............. *A61K 31/4965* (2013.01); *C12Q 1/34* (2013.01); *C07D 241/24* (2013.01); *C07D 213/83* (2013.01); *A61K 38/005* (2013.01); *A61K 31/455* (2013.01); *A61K 31/166* (2013.01); *C07D 213/81* (2013.01); *G01N 2500/02* (2013.01)
USPC ...... 514/346; 514/255.06; 514/354; 514/355; 514/357; 546/313; 546/316; 546/323; 435/18; 435/228; 548/184; 548/186; 548/188; 548/189; 548/191; 549/479; 549/478; 549/480; 549/483; 549/487

(58) Field of Classification Search
CPC .............. A61K 31/166; A61K 31/455; A61K 31/4965; A61K 38/005; C07D 213/81; C07D 213/83; C07D 241/24; C12Q 1/34; G01N 2500/02
USPC .................... 514/255.06, 354, 346, 355, 357; 546/313, 316, 323; 435/18, 228; 548/184, 186, 188, 189, 191, 193, 194, 548/198, 200, 537; 549/478, 479, 480, 483, 549/487
See application file for complete search history.

(56) References Cited

U.S. PATENT DOCUMENTS

| | | |
|---|---|---|
| 6,294,186 B1 | 9/2001 | Beerse et al. |
| 6,905,674 B2 | 6/2005 | L'Alloret |

(Continued)

FOREIGN PATENT DOCUMENTS

| | | |
|---|---|---|
| EP | 1 283 033 B1 | 2/2008 |
| JP | 2004123554 A | 4/2004 |

OTHER PUBLICATIONS

Minor et al., entitled "Synthesis of 2- and 6-Fluoronicotinamides," Chem Abstr., Journal of the American Chemical Society, 1949, vol. 71, pp. 1125-1126, abstract.

(Continued)

*Primary Examiner* — Savitha Rao
(74) *Attorney, Agent, or Firm* — Amster, Rothstein & Ebenstein LLP

(57) ABSTRACT

Compounds are disclosed which inhibit SIR2 base exchange more than deacetylation, thus enhancing SIR2 deacetylation activity. Methods of using the compounds for enhancing SIR2 deacetylation activity and increasing longevity of an organism are also disclosed. Methods for screening for compounds that enhance SIR2 deacetylation activity and increase longevity of an organism are additionally disclosed.

13 Claims, 10 Drawing Sheets

(56) References Cited

U.S. PATENT DOCUMENTS

| | | |
|---|---|---|
| 6,987,091 B2 | 1/2006 | Schramm et al. |
| 7,022,680 B2 | 4/2006 | Sauve et al. |
| 7,056,894 B2 | 6/2006 | Sauve et al. |
| 7,432,246 B2 | 10/2008 | Schramm et al. |
| 7,504,489 B2 | 3/2009 | Sauve et al. |
| 7,741,295 B2 | 6/2010 | Schramm et al. |
| 8,084,049 B2 | 12/2011 | Weidner |
| 2004/0005574 A1 | 1/2004 | Guarente et al. |
| 2006/0089318 A1 | 4/2006 | Sauve et al. |
| 2006/0094670 A1 | 5/2006 | Sauve et al. |
| 2006/0110415 A1 | 5/2006 | Gupta |
| 2010/0015072 A1 | 1/2010 | Polla et al. |

OTHER PUBLICATIONS

Althaus et al., The Journal of Biological Chemistry, vol. 257, No. 10, 1982, pp. 5528-5535.

Ogata et al., BioSci. Biotechnol. Biochem., 62 (12), 1998, pp. 2351-2356.

SCHEME I

SIR2 REGULATION

CROSS-REFERENCE TO RELATED APPLICATION

This application is a continuation of U.S. patent application Ser. No. 10/560,676, now U.S. Pat. No. 8,383,653, which is a national stage entry under 35 U.S.C. §371 of PCT International Patent Application No. PCT/US2004/020902, filed Jun. 30, 2004, which claims the benefit of U.S. Provisional Patent Application No. 60/484,321, filed Jul. 2, 2003, the contents of which are incorporated herein by reference in their entirety.

STATEMENT OF GOVERNMENT SUPPORT

This invention was made with government support under Grant No. AI34342 awarded by the National Institutes of Health. The government has certain rights in the invention.

BACKGROUND (1) Field of the Invention

The present invention generally relates to methods and compositions for increasing enzyme activities. More particularly, the invention provides methods and compositions useful for increasing SIR2 deacetylation activity.

(2) Description of the Related Art

REFERENCES CITED

Anderson, R. M., Bitterman, K. J., Wood, J. G., Medvedik, O., and Sinclair, D. A. (2003) *Nature* 423, 181-185.
Anderson, R. M., Bitterman, K. J., Wood, J. G., Medvedik, O., Cohen, H., Lin, S. S., Manchester, J. K., and Gordon, J, I. (2002) *J. Biol. Chem.* 277, 18881-18890.
Astrom, S. U., Cline, T. W., and Rine, J. (2003) *Genetics* 163, 931-937.
Bell, S. D., Botting, C. H., Wardleworth, B. N., Jackson, S. P., and White, M. F. (2002) *Science* 296, 148-51.
Berti, P. J., and Schramm, V. L. (1997) *J. Am. Chem. Soc.* 119, 12069-12078.
Bitterman, K. J., Anderson, R. M., Cohen, H. Y., Latorre-Esteves, M., and Sinclair, D. A. (2002) *J. Biol. Chem.* 277, 45099-45107.
Brachmann, C. B., Sherman J. M., Devine, S. E. Corneron, E. E. Pubs, L., and Boeke, J. D. (1995) *Genes Dev* 9, 2888-2902.
Braunstein, M., Rose, A. B., Holmes, S. C., Allis, C. D., and Broach, J. R. (1993) *Genes Dev.* 7, 592-604.
Campisi, J. (2000) *Science* 289, 2062-2063
Gasch, A. P., Spellman, P. T., Kao, C. M., Carmel-Harel, O., Eisen, M. B., Storz, G., Botstein, D., and Brown, P. O. (2000) *Mol. Biol. Cell* 11, 4241-4257.
Grozinger, C. M. et al. (2001) *J. Biol. Chem.* 276, 38837-38843.
Howitz, K. T. et al, (2003) *Nature* 425, 191-196.
Imai, S., Armstrong, C. M., Kaeberlain, M., and Guarente, L. (2000) *Nature* 403, 795-800.
Jackson, M. D., and Denu, J. M. (2002) *J. Biol. Chem.* 277, 18535-44.
Knapp, S., Vocadlo, D., Gao, Z., Kirk, B., Lou, J., and Withers, S. G (1996) *J. Am. Chem. Soc.* 118, 6804-6805.
Landry, J., Sutton, A., Tafrov, S. T., Heller, R. C., Stebbins, J., Pillus, L., and Sternglanz, (2000a) *Proc. Natl. Acad. Sci. USA* 97, 5807-5811.
Landry, J., Slama, J. T., and Sternglanz R. (20006) *Biochem. Biophys. Res. Commun.* 278, 685-690.
Lin, S. J., and Guarente, L. (2002) *Nature* 418, 344-348.
Lin S. J., Deffossez, P. A., and Guarente, L. (2000) *Science* 289, 2126-2128.
Luo, J., Nikolaev, A. Y., Imai, S., Chen, D., Su, F., Shiloh, A., Guarente, L., and Gu, W. (2001) *Cell* 107, 137-48.
Min, J., Landry, J., Sternglanz, R., and Xu, R. M. (2001) *Cell* 105, 269-279.
Minor, J. T. (1949) *J. Am. Chem. Soc.* 71, 1125-1126.
North, B. J., Marshall, B. L., Borra, M. T., Denu, J. M., and Verdin, E. (2003) *Mol Cell.* 2, 437-444.
Rine, J., and Herskowitz, I. (1987) *Genetics* 116, 9-22.
Rusche, L. N., Kirchmaier, A. L., and Rine, J. (2003) *Annu. Rev. Biochem.* 72, 481-516.
Sauve, A. A., Munshi, C., Lee, H. C., and Schramm, V. L., (1998) *Biochemistry* 37, 13239-13249
Sauve, A. A., Deng, H., Angeletti, R. H., and Schramm, V. L. (2000) *J. Am. Chem. Soc.* 122, 7855-7859.
Sauve, A. A., Celic, I., Avalos, J., Boeke, J. D., and Schramm, L. (2001) *Biochemistry* 40, 15456-15463.
Scheuring, J., and Schramm, V. L. (1997) *Biochemistry* 36, 4526-4534.
Sherman, J. M. et al. (1999) *Mol. Biol. Cell.* 10, 3045-59.
Sinclair, D. A. (2002) *Mech. Aging Dev.* 123, 857-867.
Smith, J. S., Brachmann, C. B., Celic, I., Kenna, M. A., Muhammad, S., Starai, V. J., Avalos, J. L., Escalente-Semerena, J. C., Grubmeyer, C., Wolberger, C., and Boeke, J. D. (2000) *Proc. Natl. Acad. Sci. USA* 97, 6658-6663.
Starai, V. J., Celic, I., Cole, R. N., Boeke, J. D., and Escalante-Semerena, J. C. (2003) *Science* 298, 2390-2392.
Tanner, K, G., Landry, J., Sternglanz, R., and Dean, J. M. (2000) *Proc. Natl. Acad. Sci. USA* 97, 14178-14182.
Tanny, J. C., and Moazed, D. (2001) *Proc. Natl. Acad. Sci. USA* 98, 415-20.
Tissenbaum, H. A. and Guarente, L. (2000) *Nature* 410, 227-230.
Vaziri, H., Dessain, S. K., Eaton, E. N., Imai, S. I., Frye, R., A., Pandita, T., K., Guarente, L., and Weinberg, R., A. (2001) *Cell* 107, 149-159.
Zechel, D. L., and Withers, S. G. (2000) *Acc. Chem. Res.* 33, 11-18.

The SIR2 (Silent Information Regulator) enzymes (also known as sirtuins) make up a newly classified family of $NAD^+$-dependent protein deacetylases that employ metabolically valuable $NAD^+$ as a substrate to convert acetyllysine sidechains to unmodified lysine sidechains in protein co-substrates (Landry et al., 2000a; Imai et al., 2000). The yeast SIR2 proteins were originally identified as co-regulators of genetic silencing and are localized at chromatin in protein modules called SIR complexes. Within SIR complexes these enzymes are believed to regulate chromatin structure (Smith et al., 2000; Rine & Herskowitz, 1987) by establishment and maintenance of hypoacetylation at H3 and H4 histone N-terminal tails (Rusche et al., 2003; Anderson et al., 2003; Braunstein et al., 1993). The role of these enzymes in regulating genetic information as part of a potent DNA-repressing machinery emphasizes their importance to the cell. Indeed, the SIR2 enzymes are broadly distributed across all phyla of life (Brachmann et al., 1995; Smith et al., 2000) and appear to have roles in the regulation of lifespan (Lin et al., 2000; Tissenbaum & Guarente, 2000) and genomic stability (Brachmann et al., 1995). For example, SIR2 has been identified as essential to lifespan extension caused by calorie restriction in *S. cerevisiae* (Lin at al., 2000), *C. elegans* (Tissenbaum & Guarente, 2000) and impacts lifespan in *Drosophila* (Astrom et al., 2003). Lifespan extension is caused by an increase of SIR2 activity during calorie restriction since additional copies of SIR2 genes confer an increased longevity phenotype in *S. cerevisiae* (Lin et al., 2000) and in *C. elegans* (Tissenbaum & Guarente, 2000). Since calorie restriction also confers benefits associated with increased lifespan in mammals, including primates (Lin et al., 2000), increased SIR2 activity likely leads to increased longevity in mammals.

The mechanism by which SIR2 is activated by caloric restriction is not well understood, but increased $NAD^+$/NADH ratio or increased $NAD^+$ concentration have been suggested (Lin & Guarente, 2002; Canipisi, 2000). A role for nicotinamide and the gene PNC1 in regulating SIR2 activity has also been demonstrated (Anderson et al., 2003; Bitterman et al., 2002; Anderson et al., 2002). PNC1 deamidates nicotinamide to form nicotinic acid and can lower levels of nicotinamide formed as a product of SIR2 and in pathways of $NAD^+$ metabolism (Anderson et al., 2003; Bitterman et al., 2002; Anderson or al., 2002). PNC1 is overexpressed in several stress conditions (Anderson et al., 2002; Sinclair, 2002) that increase longevity in yeast, implying that increased PNC1 activity increases SIR2 action by reducing nicotinamide inhibition. Nicotinamide is a potent inhibitor of SIR2 enzyme activity (Bitterman et al., 2002; Landry et al., 2000b) and also serves as a base-exchange substrate of SIR2 enzymes (Landry et al., 2000b; Min et al., 2001; Sauve et al., 2001). The relationship between nicotinamide base-exchange, nicotinamide inhibition and the reaction mechanism of SIR2 has not been defined, but is fundamental to regulation of SIR2 vivo.

Further characterization of the SIR2 reaction mechanism is needed to help determine ways that the deacetylation reaction could be enhanced. The present invention satisfies that need, and identifies various compounds that promote the deacetylation reaction in the presence of otherwise inhibiting amounts of nicotinamide.

SUMMARY OF THE INVENTION

Accordingly, the present invention is based on the discovery that the deacetylation reaction of SIR2 can be enhanced by compounds that inhibit base exchange more than deacetylation. It is believed that the compounds displace nicotinamide from the SIR2 enzymatic site without participating in the base exchange reaction.

Thus, in some embodiments, the invention is directed to compounds that inhibit base exchange more than deacetylation by a Sir2 enzyme, in a pharmaceutically acceptable excipient. In these embodiments, the compound has a chemical structure of one of Formula I, Formula II, Formula III, Formula IV, and Formula V, wherein Formula I has one of Structures 1-8:

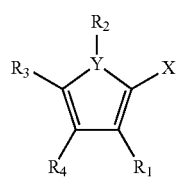

1

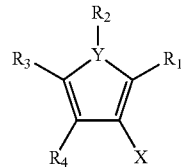

2

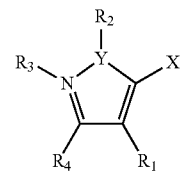

3

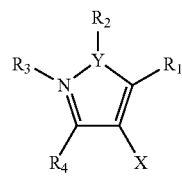

4

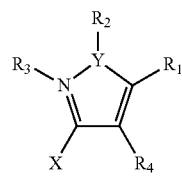

5

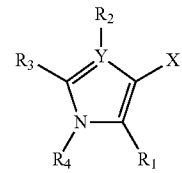

6

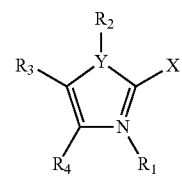

7

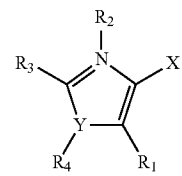

8 where $R_1$, $R_2$, $R_3$, and $R_4$ are independently H, F, CL, Me, OH, $NH_2$, $CF_3$, or Me; X is CONHMe, $COCH_3$, $COCH_2CH_3$, $COCF_3$, $CH_2OH$ or $CH_2NH_2$; and Y is N, O, or S; when Y=S or O, the corresponding R is not defined;

Formula II has one of Structures 9-18:

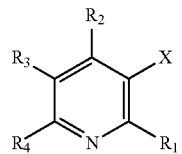
9

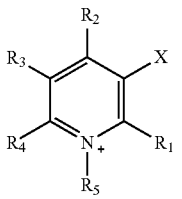
10

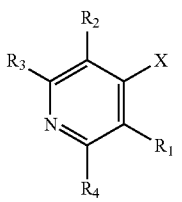
11

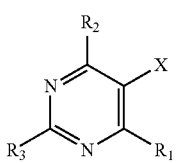
12

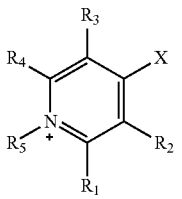
13

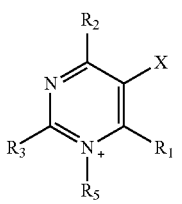
14

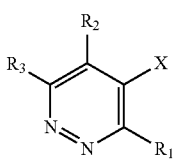
15

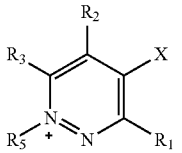
16

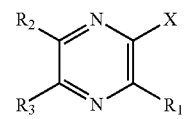
17

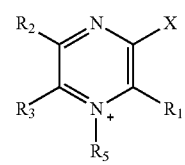
18 where $R_1$, $R_2$, $R_3$ and $R_4$ are independently H, F, Cl, OH, $NH_2$, Me or $CF_3$; X is $CONH_2$, CONHMe, $COCH_3$, $COCH_2CH_3$, $COCF_3$, $CH_2OH$ or $CH_2NH_2$; and $R_5$ is Me, $CF_3$, O or $NH_2$, and wherein Formula II is not nicotinamide;

Formula III has one of Structures 19 or 20:

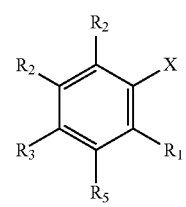
19

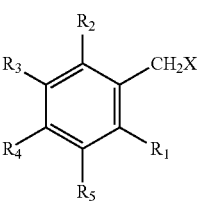
20 where $R_1$, $R_2$, $R_3$, and $R_4$, are independently H, F, Cl, OH, $NH_2$, Me or $CF_3$; and X is $CONH_2$, CONHMe, $COCH_3$, $COCH_2CH_3$, $COCF_3$, $CH_2OH$ or $CH_2NH_2$;

Formula IV has one of Structures 21 or 22:

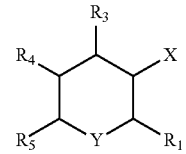
21

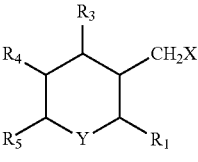
22 where the ring may comprise zero, one or two double bonds; $R_1$, $R_2$, $R_3$, and $R_4$ are independently H, F, Cl, OH, $NH_2$, Me or $CF_3$; and X is $CONH_2$, CONHMe, $COCH_3$, $COCH_2CH_3$, $COCF_3$, $CH_3OH$ or $CH_2NH_2$, and Y is N, O or S; and Formula V has one of Structures 23 or 24:

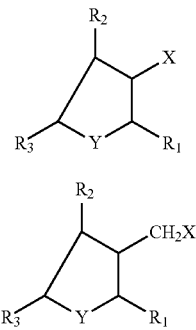

where the ring may comprise zero or one double bond; $R_1$, $R_2$, and $R_3$ are independently H, F, Cl, OH, $NH_2$, Me or $CF_3$; and X is $CONH_2$, CONHMe, $COCH_3$, $COCH_2CH_3$, $COCF_3$, $CH_2OH$ or $CH_2NH_2$; and Y is N, O or S.

In other embodiments, the invention is directed to methods of inhibiting base exchange more than deacetylation of an acetylated peptide by a Sir2 enzyme. The methods comprise combining a compound with the Sir2 enzyme, $NAD^+$ and the acetylated peptide. In these methods, the compound is one of the above compounds.

The invention is additionally directed to methods for increasing longevity in an organism. The methods comprise treating the organism with one of the above compounds.

In further embodiments, the invention is directed to methods of increasing protein deacetylation by a Sir2 enzyme in a living cell. The methods comprise combining the cell with one of the above compounds.

The invention is further directed to methods of increasing deacetylation activity of a Sir2 enzyme. The methods comprise combining one of the above compounds with the Sir2 enzyme, $NAD^+$ and an acetylated peptide substrate of the Sir2.

In other embodiments, the invention is directed to methods of inhibiting base exchange more than deacetylation of an acetylated peptide by a Sir2 enzyme. The methods comprise displacing nicotinamide from a Sir2 enzymatic site, using one of the above compounds.

The invention is also directed to methods of screening a test compound for the ability to increase Sir2 deacetylation activity. The methods comprise combining the test compound with the Sir2 enzyme, $NAD^+$ and an acetylated peptide substrate of Sir2 in a reaction mixture, and determining whether the compound prevents base exchange more than deacetylation.

Additionally, the invention is directed to methods of screening a test compound for the ability to increase longevity in an organism. The methods comprise combining the test compound with a Sir2 enzyme, $NAD^+$ and an acetylated peptide substrate of the Sir2 in a reaction mixture, and determining whether the compound prevents base exchange more than deacetylation.

In further embodiments, the invention is directed to methods of determining whether a compound increases deacetylation activity of a SIR enzyme in a cell. The methods comprise comparing the expression of a reporter gene between the cell when not exposed to the compound and the cell when exposed to the compound, where the reporter gene is integrated at a chromosomal locus in the cell that is subject to transcriptional silencing by the SIR enzyme, and where decreased expression of the reporter gene in the cell exposed to the compound indicates the compound increases deacetylation activity of the SIR in the cell.

[14C]nicotinamide concentration. Panel a shows nicotinamide base exchange rate measured at different concentrations of isonicotinamide. The increase in apparent $K_m$ for exchange is due to competitive inhibition by isonicotinamide with nicotinamide binding. Concentrations of isonicotinamide are 0, 60 and 100 mM and $K_m$ values are 120, 190 and 250 μM respectively as determined from best fits of the points to the Michaelis-Menton Equation. Panel b shows deacetylation rate measured as a function of $^{14}C$-nicotinamide concentration in reactions containing the same isonicotinamide concentrations used in panel a. Inhibition curves are fit to the equation for partial inhibition: relative rate=1−f([I]/($K_i$+[I])) where relative rate is defined on a scale of 1 based on the uninhibited rate. The constant f is the fractional inhibition attained by nicotinamide saturation. [I] is the concentration of nicotinamide and $K_i$ is the apparent nicotinamide inhibition constant (Sauve and Schramm, 2003). The $K_i$ values of 100, 180 and 330 μM for 0, 60 and 100 mM isonicotinamide reflect binding competition between nicotinamicie, an inhibitor of deacetylation, and isonicotinamide, winch is not an inhibitor. Panel c shows base exchange and deacetylation rates measured as a function of isonicotinamide concentration at a fixed, physiologically relevant concentration of nicotinamide (125 μM), which is inhibitory for Sir2-catalyzed deacetylation ($k_i$=100 μM). Measurements were performed by methods described in Sauve and Schramm (2003) with the H4N-terminal peptide (AGG(AcK)GG(AcK)GMG(AcK)VGA(AcK)RHSC) (Imai et al., 2000) as substrate.

Figure 8:
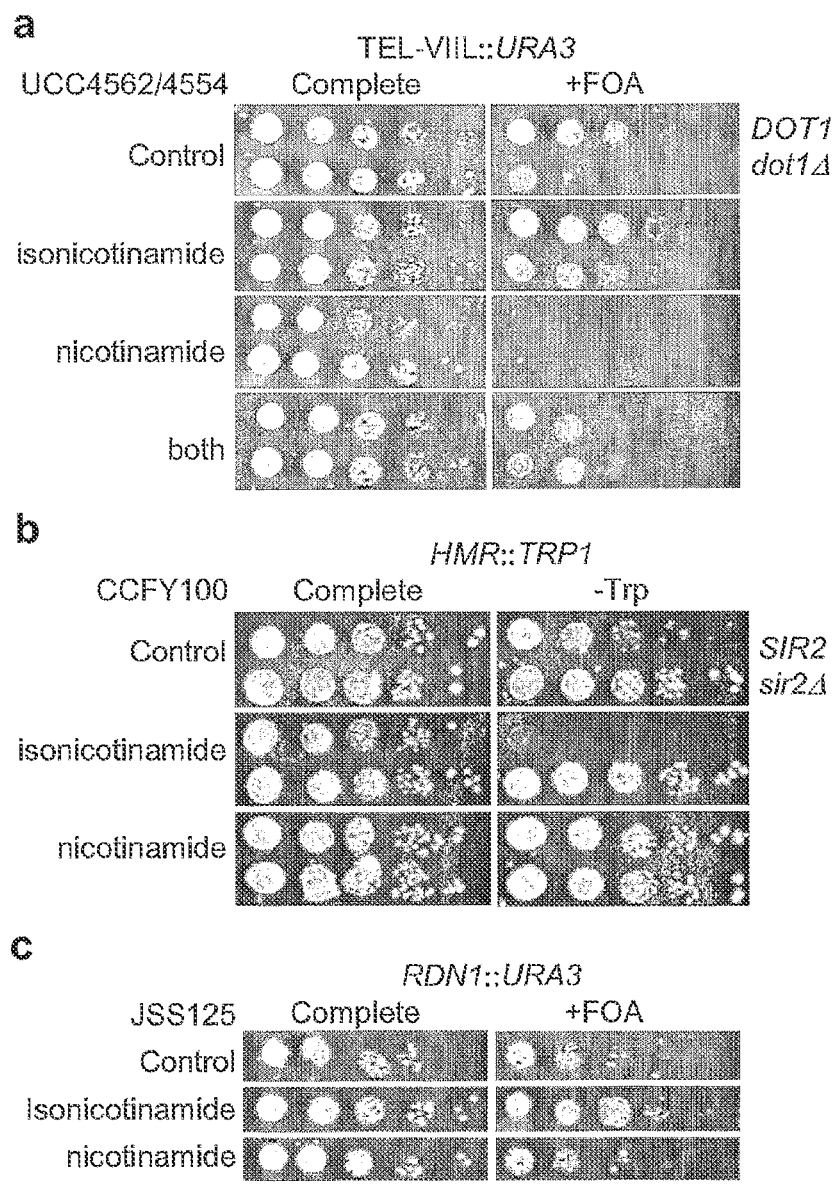

FIG. 8 is photographs of experimental results demonstrating that isonicotinamide increases silencing at Sir2-regulated loci. Ten-fold serial dilutions of yeast strains were spotted onto control (YPD) or selective media (vanLeeuwen and Gottschling, 2002). The photographs were taken after 2 to 3 days incubation. Test media contained 25 mM isonicotinamide, 5 mM nicotinamide or both compounds. Panel a shows silencing at telomere VIIL, monitored by URA3 expression through increased survival on media containing FOA. Isogenic strains UCC4562 (DOT1) and UCC4554 (dot1Δ) (Singer et al., 1998) are shown in each panel (top and bottom rows, respectively). Panel b shows silencing at the HMR locus was detected by TRP1 expression through decreased survival on media lacking tryptophan. The phenotype of strain CCFY10028 (top row) is compared to an isogenic sir2 derivative (bottom row). The sir2 deletion strain was generated by PCR-mediated gene disruption using a Nat-MX selectable marker (Tong et al., 2004). Panel c shows silencing of URA3 expression at the rDNA locus of strain JSS125(S3) 30 was assayed on FOA-containing media.

Figure 9:
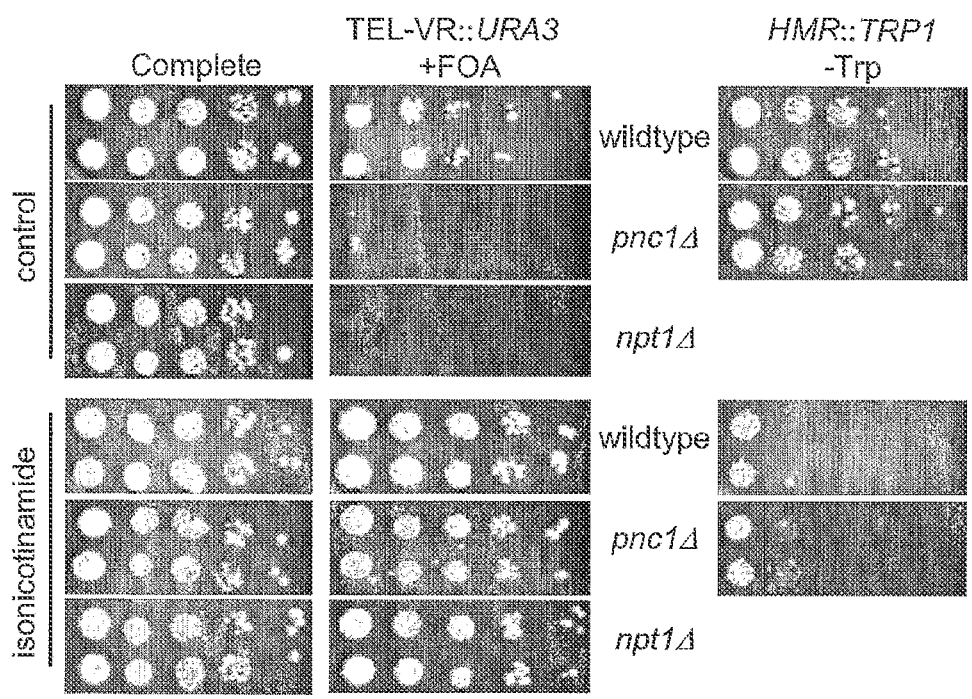

FIG. 9 is photographs of experimental results demonstrating that activation of silencing by isonicotinamide does not require PNC1 or NPT1. Ten-fold serial dilutions of strain CCFY100 and isogenic npt1 and pnc1 derivatives were spotted onto YPD or selective media with or without 25 mM isonicotinamide. The deletion strains were generated by PCR-mediated gene disruption using a Nat-MX selectable marker (Tong et al., 2004). Silencing at TEL-VR::URA3 is reported by survival on FOA-containing media and at HMR::TRP1 is detected by reduced growth on media lacking tryptophan.

Figure 10:
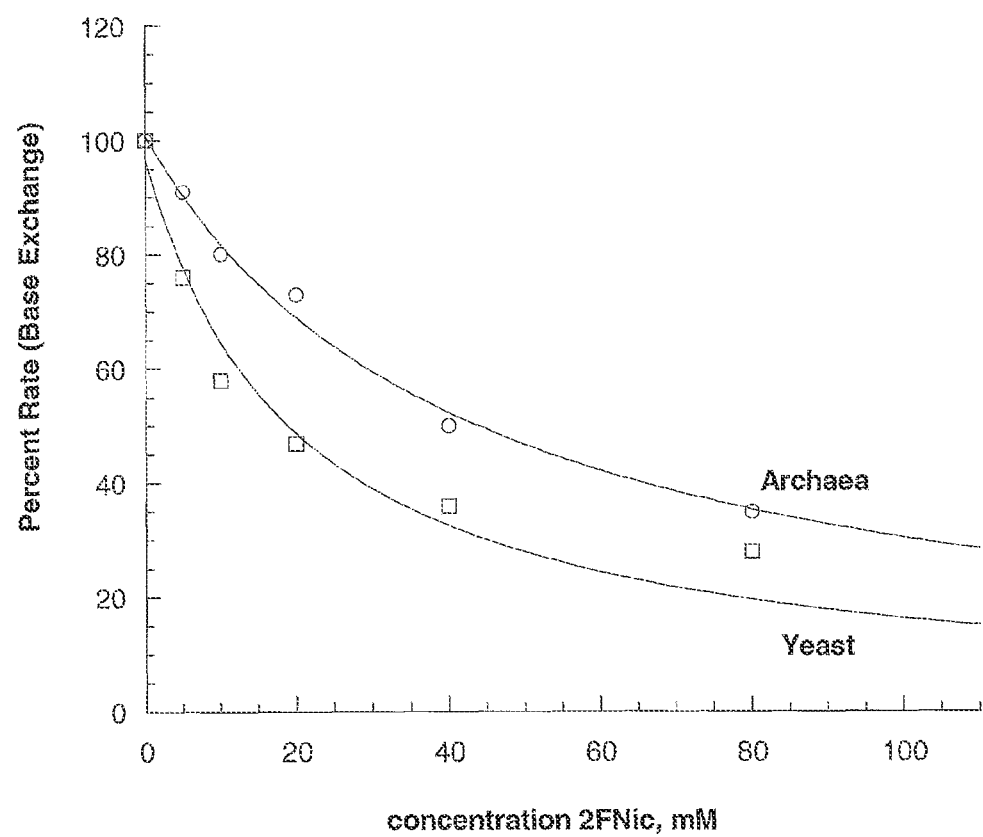

FIG. 10 shows the inhibition of base exchange catalyzed by archaea and yeast enzymes as a function of 2-fluoronicotinamide concentration. The curves are best fits to the points using the equation 100−100*([I]/([I]+$K_i$))=Percent rate. Where [I] is the concentration of the inhibitor and $K_i$ is the inhibitor binding constant. These curves give a 20 mM binding constant for Sir2p (yeast) and a 43 mM binding constant for Af2Sir2 (archaean).

DETAILED DESCRIPTION OF THE INVENTION

The present invention is based on the discovery that SIR2 base exchange can be inhibited more than deacetylation. Compounds that inhibit base exchange more than deacetylation have also been identified. Those compounds promote a net increase in deacetylation, thus effectively increasing the deacetylation activity of SIR2.

Thus, in some embodiments, the invention is directed to compounds that inhibit base exchange more than deacetylation by a SIR2 enzyme. Without being limited to any particular mechanism, the compounds are believed to inhibit base exchange by displacing nicotinamide from the SIR2 active site. Therefore, the preferred compounds have structural characteristics similar to nicotinamide, for example the following structures of Formula I, Formula II, Formula III, Formula IV, and Formula V, where Formula I has one of Structures 1-8:

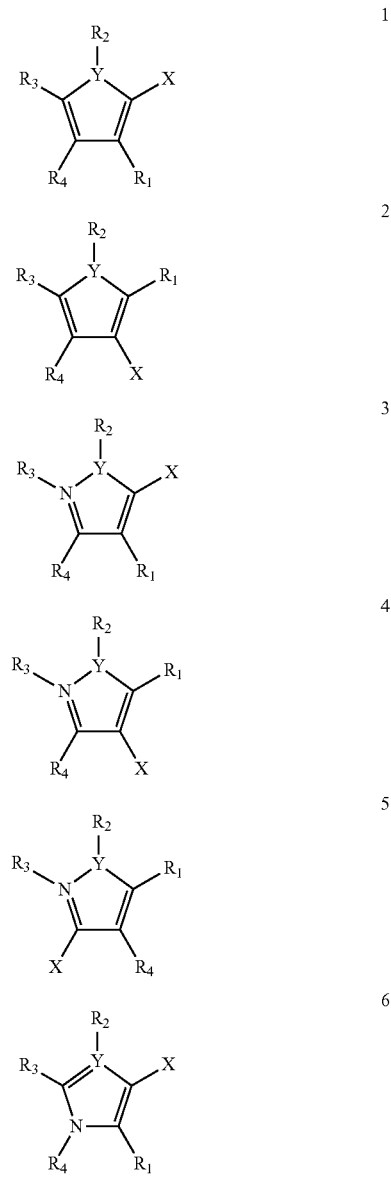

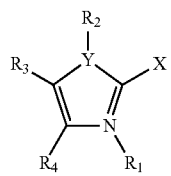
7

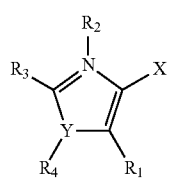
8 where $R_1$, $R_2$, $R_3$ and $R_4$ are independently H, F, Cl, Me, OH, NH$_2$, CF$_3$ or Me; X is CONHMe, COCH$_3$, COCH$_2$CH$_3$, COCF$_3$, CH$_2$OH or CH$_2$NH$_2$; and Y is N, O, or S; when Y=S or O, the corresponding R is not defined;

Formula II has one of Structures 9-18:

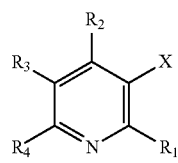
9

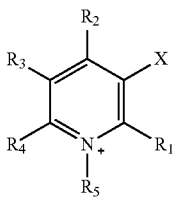
10

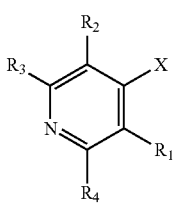
11

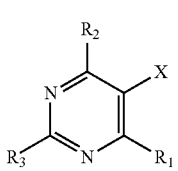
12

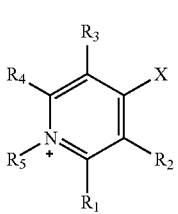
13

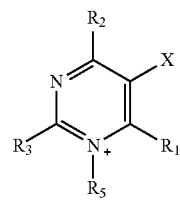
14

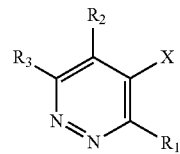
15

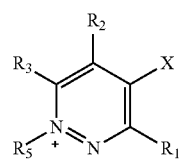
16

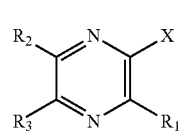
17

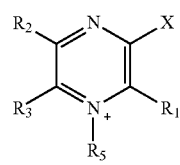
18 where $R_1$, $R_2$, $R_3$ and $R_4$ are independently H, F, Cl, OH, NH$_2$, Me or CF$_3$; X is CONH$_2$, CONHMe, COCH$_2$, COCH$_2$CH$_3$, COCF$_3$, CH$_2$OH or CH$_2$NH$_2$; and $R_5$ is Me, CF$_3$, O or NH$_2$, and wherein Formula II is not nicotinamide;

Formula III has one of Structures 19 or 20:

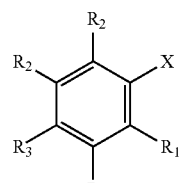
19

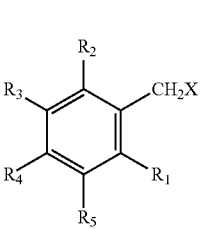
20 where $R_1$, $R_2$, $R_3$, $R_4$, and $R_5$ are independently H, F, Cl, OH, NH$_2$, Me or CF$_3$; and X is CONH$_2$, CONHMe, COCH$_2$, COCH$_2$CH$_3$, COCF$_3$, CH$_2$OH or CH$_2$NH$_2$;

Formula IV has one of Structures 21 or 22:

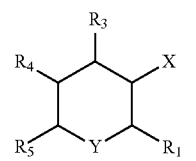

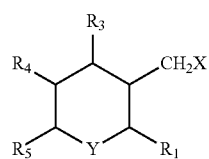

where the ring may comprise zero, one or two double bonds; $R_1$, $R_2$, $R_3$, and $R_4$ are independently H, F, Cl, OH, $NH_2$, Me or $CF_3$; and X is $CONH_2$, CONHMe, $COCH_3$, $COCH_2CH_3$, $COCF_3$, $CH_2OH$ or $CH_2NH_2$; and Y is N, O or S; and Formula V has one of Structures 23 or 24:

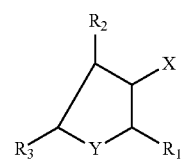

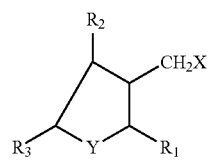

where the ring may comprise zero or one double bond; $R_1$, $R_2$, and $R_3$ are independently H, F, Cl, OH, $NH_2$, Me or $CF_3$; and X is $CONH_2$, CONHMe, $COCH_3$, $COCH_2CH_3$, $COCF_3$, $CH_2OH$ or $CH_2NH_2$; and Y is N, O or S.

Preferably, the compound has one of structures 1, 2, 6, 21, 22, 23 or 24, where X is $CONH_2$ and Y is N; Structure 9, where at least one of $R_1R_4$ is F and X is $CONH_2$; Structure 11, where $R_1$, $R_2$, $R_3$ and $R_4$ are independently H or F and X is $CONH_2$; or Structures 19 and 20, where at least one of $R_1$-$R_5$ is F and X is $CONH_2$.

More preferably, the compound has one of Structure 1 or 2, where $R_2$ is $CH_3$, and $R_1$, $R_3$ and $R_4$ is H; Structure 6, where $R_1$, $R_3$ and $R_4$ is H and $R_2$ is $CH_3$ or H; Structure 9, where $R_1$ is F, $R_2$-$R_4$ is H, and X is $CONH_2$ (2-fluoronicotinamide); other fluoronicotinamides, or Structure 11, wherein $R_1$-$R_4$ is H and X is $CONH_2$ (isonicotinamide). Example 1 provides data showing that isonicotinamide inhibits base exchange more than deacetylation of the *S. cerevisiae* SIR2p enzyme; Example 3 provides data showing that 2-fluoronicotinamide inhibits base exchange more than deacetylation of a yeast and an archaeal SIR2 enzyme. In most preferred embodiments, the compound is isonicotinamide or a fluoronicotinamide such as 2-fluoronicatinamide.

The compounds that inhibit SIR2 base exchange more than deacetylation can be used in various methods for increasing SIR2 deacetylation activity. In some embodiments, the invention is directed to methods of inhibiting base exchange more than deacetylation of an acetylated peptide by a SIR2 enzyme. The methods comprise combining the SIR2, enzyme, $NAD^+$ and the acetylated peptide with a compound that inhibits SIR2 base exchange more than deacetylation. Preferably, the compound is one of the above described compounds of Formula or Formula where the most preferred compounds are as described above.

These methods would be expected to be useful for inhibiting base exchange more than deacetylation of any acetylated peptide SIR2 substrate. As is known; SIR2s are capable of deacetylating any peptide of at least two amino acids, provided the peptide has a lysine residue acetylated at the ε-amino moiety, including p53, histones, and small peptides (see, e.g., PCT/US02137364 and references cited therein).

The SIR2 enzyme can also be derived from any species, including a prokaryotic, archeal, or eukaryotic (including mammalian) source. Nonlimiting examples of SIR2 enzymes useful for these methods are Sir2Af2 (*Archaeoglobus fulgidus*), Sir2Tm (*Thermotoga maritima*), cobB (*Salmonella typhimurium*), Sir2p (*Saccharomyces cereviseae*), SIR2α, (mouse), and Sir2A, SIRT1, SIRT2, SIRT3, SIRT4, SIRT5, SIRT6, SIRT7, SIRT2p, and SIRT1p (human).

In some embodiments, the method is performed in vitro, i.e., the SIR2 enzyme, $NAD^+$ and the acetylated peptide are combined in a reaction mixture outside of a living cell.

In other embodiments, the method is performed in a living cell, by adding the compound to a living cell that also has the SIR2 enzyme, the $NAD^+$ and the acetylated peptide. In these in vivo embodiments, the SIR2 enzyme can be native to the cell, or can be introduced, e.g., by transfecting the cell with an expression vector comprising a nucleic acid sequence encoding the SIR2 enzyme, by any method known in the art. The living cell can be an archaeal cell, a prokaryotic cell or a eukaryotic cell, including a mammalian cell. In some aspects of these in vivo embodiments, the cell is part of a living multicellular organism, e.g., a mammal such as a mouse or a human.

Since increases of SIR2 deacetylation activity are associated with increases in longevity in a wide variety of organisms (Lin et al., 2000), methods that increase the effective SIR2 deacetylation activity in an organism would be expected to increase the lifespan of that organism.

The invention is therefore directed to methods of increasing longevity in an organism. The methods comprise treating the organism with a compound that SIR2 base exchange more than deacetylation. Preferred and most preferred compounds are from Formula I or Formula II, as described above.

As with previously described in vivo embodiments, the SIR2 enzyme that is targeted in the organism can be a native SIR2 or it can be transfected into the organism such that the organism expresses a recombinant SIR2. Also as with previously described in vivo embodiments, the organism can be any prokaryote, archaea, or eukaryote, including fungi (e.g., Yeasts), insects (e.g., fruit flies), or mammals such as mice or humans.

In related embodiments, the invention is also directed to methods of increasing protein deacetylation by a SIR2 enzyme in a living cell. The methods comprise combining the cell with a compound that inhibits SIR2 base exchange more than deacetylation. The preferred compounds are as previously discussed, i.e., those of Formula I and II, as described above. Also as with previous embodiments, the cell can be prokaryotic, archaeal, or a eukaryote, for example a yeast cell or a mammalian cell, including from a mouse or a human. The cell can also be in culture or as part of a living multicellular organism.

In other related embodiments, the invention is additionally directed to methods of increasing deacetylation activity of a SIR2 enzyme. The methods comprise combining the SIR2 enzyme, NAD$^+$ and an acetylated peptide substrate of the SIR2 with a compound that inhibits SIR2 base exchange more than deacetylation. As with the previously described embodiments, the preferred compounds are those of Formula I and Formula II, as described above. The enzyme can also be any SIR2 known, including prokaryotic, archaeal or eukaryotic SIR2s, such as mouse SIR2α and human Sir2A, SIRT1, SIRT3, SIRT5, SIRT6, SIRT7, SIRT2p, and SIRT1p. Also as with previous embodiments, the method can be performed in vitro, i.e., in a reaction mixture outside of a living cell, or in vivo, where the SIR2 enzyme is in a living cell. In the latter embodiments, the cell can be part of a living organism, analogous to previously discussed embodiments.

In related embodiments, the invention is directed to methods of inhibiting base exchange more than deacetylation of an acetylated peptide by a SIR2 enzyme. The methods comprise displacing nicotinamide from a SIR2 enzymatic site, preferably using a compound of Formula I or Formula II. Since it is believed that the Formula I and Formula II compounds inhibit SIR2 base exchange more than deacetylation by displacing nicotinamide form the SIR2 enzymatic site, this method is entirely analogous to the previously described methods, and includes in vitro and in vivo embodiments, with any SIR2 enzyme, with the same preferred compounds, etc. as the above-described methods.

The knowledge that compounds are available that inhibit SIR2 base exchange more than deacetylation suggests methods for screening test compounds for the ability to increase SIR2 deacetylation activity. Thus, the present invention is also directed to methods of screening a test compound for the ability to increase SIR2 deacetylation activity. The methods comprise combining the test compound with the SIR2 enzyme, NAD$^+$ and an acetylated peptide substrate of SIR2 in a reaction mixture, and determining whether the compound prevents base exchange more than deacetylation. The methods are preferably performed using radiolabeled nicotinamide, e.g., by the methods described in Example 1. It should be understood that these methods could be used to quantitatively compare various compounds, e.g., those of Formula I, Formula II, Formula III, Formula IV, and Formula V for the relative efficacy in enhancing SIR2 deacetylation activity.

Based on the effect of SIR2 deacetylation activity on longevity, the screening methods described immediately above is also useful for screening compounds for the ability to increase longevity. Thus, the invention is also directed to methods of screening a test compound for the ability to increase longevity in an organism. The methods comprise combining the test compound with a SIR2 enzyme, NAD$^+$ and an acetylated peptide substrate of the SIR2 in a reaction mixture, and determining whether the compound prevents SIR2 base exchange more than deacetylation.

In these methods, the SIR2 enzyme is preferably derived from the organism. The organism can be a prokaryote, an archaea or a eukaryote, for example a yeast cell or a mammal, including a mouse or a human. The method can be used to determine the relative effect of various compounds on longevity, by quantitatively determining the relative effect of each compound on inhibition of SIR2 base exchange vs. deacetylation. Thus, the method could be used to evaluate the relative effect of, e.g., various compounds of Formula I and Formula II on longevity.

Since the compounds of the present invention are useful in the various methods described above for treating animals, including mammals such as mice and humans, it should be understood that those compounds are useful as pharmaceutical compositions. Thus, the invention is also directed to compositions comprising compounds that inhibit SIR2 base exchange more than deacetylation, in a pharmaceutically acceptable excipient. The compounds are preferably those various Formula I and Formula II compositions described above, and more preferably, the various preferred embodiments of those Formula I and Formula II compositions.

In the above-described methods involving treating an animal, the pharmaceutical composition of the compound may be administered to a human or animal subject by known procedures, including, without limitation, oral administration, parenteral administration (e.g., epifascial, intracapsular, intracutaneous, intradermal, intramuscular, intraorbital, intraperitoneal, intraspinal, intrasternal, intravascular, intravenous, parenchymatous, or subcutaneous administration), transdermal administration, and administration by osmotic pump. Preferably, the pharmaceutical composition of the present invention is administered orally.

For oral administration, the compound may be formulated in solid or liquid preparations, e.g., capsules, tablets, powders, granules, dispersions, solutions, and suspensions.

Such preparations are well known in the art as are other oral dosage forms not listed here. In a preferred embodiment, the compounds of the invention are tableted with conventional tablet bases, such as lactose, sucrose, mannitol, and cornstarch, together with a binder, a disintegration agent, and a lubricant. These excipients are well known in the art. The formulation may be presented with binders, such as crystalline cellulose, cellulose derivatives, acacia, corn starch, or gelatins. Additionally, the formulation may be presented with disintegrators, such as corn starch, potato starch, or sodium carboxymethylcellulose. The formulation also may be presented with dibasic calcium phosphate anhydrous or sodium starch glycolate. Finally, the formulation may be presented with lubricants, such as talc or magnesium stearate. Other components, such as coloring agents and flavoring agents, also may be included. Liquid forms for use in the invention include carriers, such as water and ethanol, with or without other agents, such as a pharmaceutically-acceptable surfactant or suspending agent.

For parenteral administration (i.e., administration by injection through a route other than the alimentary canal), the compound may be combined with a sterile aqueous solution that is preferably isotonic with the blood of the subject. Such a formulation may be prepared by dissolving a solid active ingredient in water containing physiologically-compatible substances, such as sodium chloride, glycine, and the like, and having a buffered pH compatible with physiological conditions, so as to produce an aqueous solution, then rendering said solution sterile. The formulations may be presented in unit or multi-dose containers, such as sealed ampules or vials. The formulation may be delivered by any mode of injection, including, without limitation, epifascial, intracapsular, intracutaneous, intradermal, intramuscular, intraorbital, intraperitoneal, intraspinal, intrasternal, intravascular, intravenous, parenchymatous, or subcutaneous.

For transdermal administration, the compound may be combined with skin penetration enhancers, such as propylene glycol, polyethylene glycol, isopropanol, ethanol, oleic acid, N-methylpyrrolidone, and the like, which increase the permeability of the skin to the compound, and permit the compound to penetrate through the skin and into the bloodstream. The compound/enhancer composition also may be further combined with a polymeric substance, such as ethylcellulose, hydroxypropyl cellulose, ethylene/vinylacetate, polyvinyl pyrrolidone, and the like, to provide the composition in gel form, which may be dissolved in solvent, such as methylene chloride, evaporated to the desired viscosity, and then applied to backing material to provide a patch. The compound may be administered transdermally, at or near the site on the subject where the disease or condition is localized. Alternatively, the compound may be administered transdermally at a site other than the affected area, in order to achieve systemic administration.

The compound of the present invention also may be released or delivered from an osmotic mini-pump or other time-release device. The release rate from an elementary osmotic mini-pump may be modulated with a microporous, fast-response gel disposed in the release orifice. An osmotic mini-pump would be useful for controlling release, or targeting delivery, of the compound.

The inventors have also developed a novel assay for deacetylase activity causing in vivo transcriptional silencing, as in SIR2 and related enzymes ("SIR enzymes"). The assay uses cells having a reporter gene integrated at a chromosomal locus in the cell that is subject to SIR transcriptional silencing. The compound is combined with the cells and the activity of the reporter gene is determined. Decreased reporter gene activity in the cells exposed to the compound indicates that the compound causes an increase in the SIR deacetylase activity, whereas increased reporter gene activity in the cells exposed to the compound indicates that the compound causes a decrease in the SIR deacetylase activity. The assay is exemplified in Example 2, where activity of native SIR2 in transgenic yeast having reporter genes that are selectable markers integrated into a SIR2 target locus. See also Grozinger et al., 2001. Example 2 demonstrates assays where increased SIR2 deacetylase activity can either enhance growth or reduce growth of yeast colonies, depending whether a positively selectable or a negatively selectable marker is used.

Thus, in additional embodiments, the invention is directed to methods of determining whether a compound affects deacetylation activity of a SIR enzyme in a cell. The methods comprise comparing the expression of a reporter gene between the cell when not exposed to the compound and the cell when exposed to the compound, wherein the reporter gene is integrated at a chromosomal locus in the cell that is subject to transcriptional silencing by the SER enzyme, and wherein decreased expression of the reporter gene indicates SIR deacetylation activity in the cell.

These methods are not limited to any particular cell, but can be used with any eukaryotic, prokaryotic or archaeal cell that has a reporter gene integrated at a chromosomal locus in the cell that is subject to transcriptional silencing by the SIR enzyme, or can be constructed to have that characteristic. In preferred embodiments, the cell is a yeast cell, such as employed in Example 2.

The reporter gene can also be utilized at any locus subject to transcriptional silencing by the SIR enzyme, for example a telomere, au rDNA array or a silent mating type locus of the cell, e.g., as in Example 2.

These methods are also not limited to the use of any particular reporter gene. The reporter gene can be detectable, e.g., by immunoassay of an antigen or epitope of the reporter gene product, or by observation or spectrophotometric measurement of color or fluorescence increase, e.g., by using green fluorescent protein or peroxidase as the reporter gene product. These embodiments lend themselves to quantitative or semi-quantitative measurement of the difference in transcriptional silencing between the cell treated with a particular compound and the cell not treated, or treated with a positive or negative control compound. Thus, relative effectiveness of the test compound vs. other compounds can be determined.

In other embodiments, the reporter gene is a selectable marker. Nonlimiting examples include an ADE2 gene, or a URA3 gene or a TRP1 gene, as in Example 2, where cell colony growth can be utilized as the marker for identifying active compounds.

The SIR enzyme utilized in these methods can be a naturally occurring in the cell or a transgenic SIR enzyme can be engineered into the cell, for example engineering a mammalian (e.g., human), or a chimeric SIR enzyme transgenically expressed in a yeast cell. See, e.g., Sherman at al. (1999; and Howitz et al. (2003).

These methods can be used with any SIR enzyme now known or later discovered, including SIR2a, SIR2A, SIRT3, SIRT2p, SIRT1p, SIRT1, SIRT2, SIRT3, SIRT4, SIRT5, SIRT6 and SIRT7.

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims, which follow the examples.

Example 1

SIR2 Regulation by Nicotinamide Results from Switching Between Base Exchange and Deacetylation Chemistry Example Summary Life span regulation and inhibition of gene silencing in yeast have been linked to nicotinamide effects on SIR2 enzymes. The SIR2 enzymes are $NAD^+$-dependent protein deacetylases that influence gene expression by forming deacetylated proteins, nicotinamide and 2'-O-acetyl-ADPR. Nicotinamide is a base-exchange substrate as well as a biologically effective inhibitor. Characterization of the base-exchange reaction reveals that nicotinamide regulates SIR2s by switching between deacetylation and base exchange. Nicotinamide switching is quantitated for the SIR2s from *Archeaglobus fulgidus* (AF2), *Saccharomyces cerevisiae* (SIR2p), and mouse (SIR2α). Inhibition of deacetylation was most effective for mouse SIR2α suggesting species-dependent development of this regulatory mechanism. The SIR2s are proposed to form a relatively stable covalent intermediate between ADPR and the acetyl-oxygen of the acetyllysine-protein substrate. During the lifetime of this intermediate, nicotinamide occupation of the catalytic site determines the fate of the covalent complex. Saturation of the nicotinamide site for mouse, yeast and bacterial SIR2s causes 95%, 65% and 21% of the intermediate, respectively, to return to acetylated protein. The fraction of the intermediate committed to deacetylation results from competition between the nicotinamicie and the neighboring T-hydroxyl group at the opposite stereochemical face. Nicotinamide-switching supports the previously proposed SIR2 catalytic mechanism and the existence of a 1'-O-peptidyl-ADPR.SIR2 intermediate. These findings suggest a strategy to increase SIR2 enzyme catalytic activity in vivo by inhibition of chemical exchange but not deacetylation.

Introduction

SIR2s have evolved a catalytically complex mechanism to involve $NAD^+$ and nicotinamide in an otherwise chemically simple N-deacetylase reaction. Reactions with peptide substrates produce the acetyl ester metabolites 2'- and 3'-O-acetyl-ADPR (Sauve et al., 2001; Jackson & Denu, 2000), nicotinamide and deacetylated lysine sidechains. The chemical mechanism that unites base exchange and deacetylation reactions arises from a covalent 1'-O-peptidylamidate-ADPR intermediate that releases nicotinamide from the active site (Sauve et al., 2001). This intermediate is sufficiently stable to permit regeneration of NAD$^+$ in the presence of elevated nicotinamide concentrations (Scheme 1A). This mechanism explains the requirement for the protein acetyllysine substrate to permit the base-exchange reaction and is consistent with all reliable information reported from active site mutagenesis studies, isotope-labeling, and X-ray crystallography (Min et al., 2001; Sauve et al., 2001; Jackson & Denu, 2002).

Here we characterize the base exchange and inhibition kinetics for SIR2 enzymes from *Archeaglobus fulgidus* (AF2), *Saccharomyces cerevisiae* (SiR2p), and mouse (SIR2α). These results establish that base exchange and nicotinamide inhibition are both consequences of the chemical reactivity of a single enzymatic intermediate. Interestingly, nicotinamide inhibition of yeast and bacterial enzyme deacetylation is incomplete at elevated nicotinamide concentrations. The inhibition patterns for all three enzymes can be explained by a reaction mechanism in which base exchange and deacetylation are competitive chemical processes emerging from the bifurcating reactivity of a SIR2 peptidyl-ADPR intermediate. This interpretation provides new insight into the chemical mechanism, reaction coordinate energetics and regulation of the SIR2 enzymes. Strategies for increasing the catalytic deacetylation activity of SIR2 are apparent from this novel mechanism.

Results

Kinetics of Nicotinamide Exchange and Inhibition.

Figure 1:
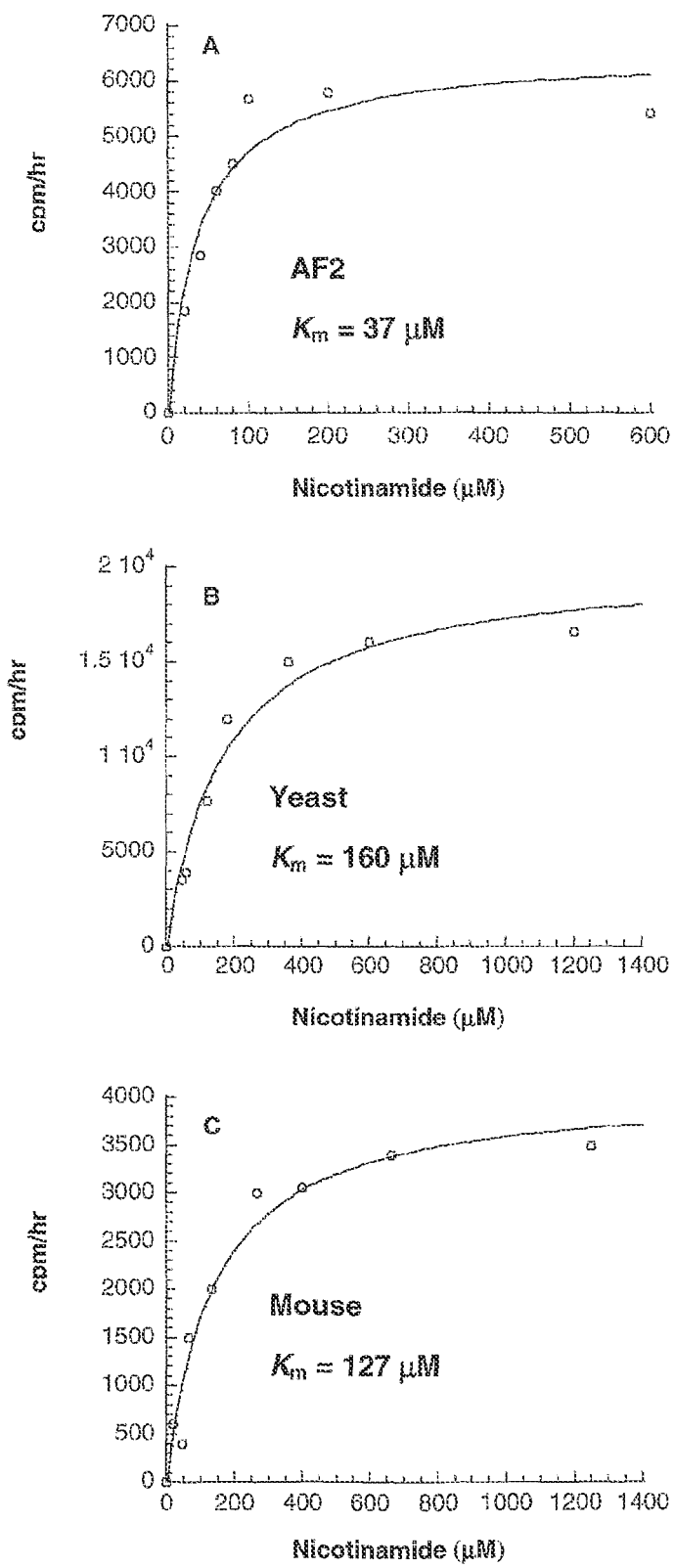
FIG. 1 shows graphs for determining the exchange reaction rates versus nicotinamide concentration for representative SID2 enzymes. Enzyme origins: Panel A, bacterial; Panel B, yeast; Panel C, mouse. The lines are fits to the Michaelis-Menten equation.
Figure 2:
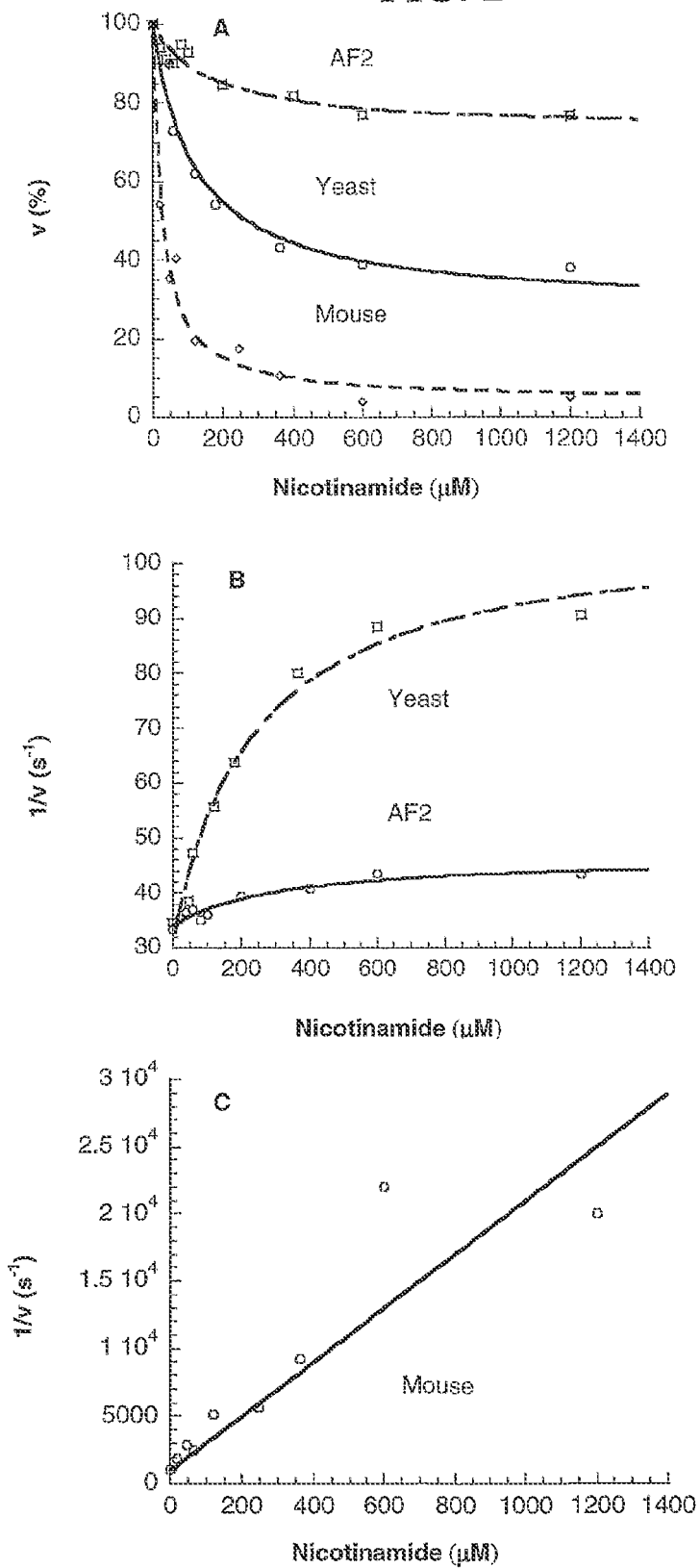
FIG. 2 shows graphs for determining the deacetylation rate of bacterial, yeast and mouse SIR2 enzymes, as a function of nicotinamide concentration. The lines were fit to the equation $v=k_{cat}-k_p([I]/K_t+[I])$ as defined in the text. The residual rate of deacetylation is the plateau (Panel A). Dixon plots (1/v versus [I]) of the deacetylation rates for yeast and AF2 enzymes (Panel B), and for mouse enzyme (Panel C). Experimental data were fit to either a linear equation (Panel C) or as defined in the text.

Several SIR2 enzymes have been shown to catalyze chemical exchange of radiolabeled nicotinamide into NAD$^+$ in the presence of an acetyllysine protein or peptide substrate (Landry et al., 2000b; Min et al., 2001; Sauve et al., 2001). However, the kinetic and chemical mechanisms of base-exchange have not been reported. Rates of SIR2 catalyzed exchange were measured as a function of [carbonyl-$^{14}$C]nicotinamide with saturating NAD$^+$ and peptide substrates (Sauve et al., 2001). The K$_m$ values for nicotinamide base exchange for the AF2, mouse and yeast SIR2 enzymes were determined to be 36 μM, 127 μM and 160 μM respectively (FIG. 1 and Table 1).

plotted as a function of the nicotinamide concentration (FIG. 2). Product formation rates decreased as nicotinamide concentrations were increased but nicotinamicie did not cause complete inhibition for the bacterial and yeast enzymes (FIG. 2A). Approximately 79% and 35% respectively of the uninhibited rates remained at millimolar concentrations of nicotinamide. For the mouse enzyme, >95% inhibition occurred at high nicotinamide concentrations (FIG. 2A). Dixon plots (1/v versus [I]) were hyperbolic for the AF2 and yeast enzymes, but linear for the mouse enzyme (FIG. 2B, C). The K$_m$ for NAD$^+$ for the three enzymes is in the range 100-200 μM for these conditions. Increases in nicotinamide concentration to 2 mM did not alter the plateau for deacetylation or exchange rates for any of the three enzymes (data not shown; error±5%), demonstrating that nicotinamide competition for NAD$^+$ binding is in excess of 8 mM.

Nicotinamide inhibition of bacterial and yeast enzymes was consistent with a non-competitive interaction at a single binding site with a dissociation constant K. Fractional inhibition occurs by saturation of the site, expressed as $v=k_{cat}-k_p([I]/K_i+[I])$ for curves of v versus I; and $1/v=1/k_{cat}-k_p([I]/K_i+[I])$ for curves 1/v versus I, where v is the rate of deacetylation, [I] is nicotinamide concentration, k$_p$ is the extent to which the deacetylation reaction is decreased when the site is saturated and k$_{cat}$ is the deacetylation reaction rate at saturating NAD$^+$ and peptide with no inhibitor present. When [I]>>K$_i$ the curve of v versus I asymptotically approaches the value $k_{inh}=k_{cat}-k_p$ (FIG. 2). Values for k$_{inh}$, the residual deacetylation rate at nicotinamide saturation, are given in Table 1. Determinations of K$_i$ allow comparison with K$_m$ (exchange) for each enzyme. These values agree within experimental error, indicating that one site governs inhibition of deacetylation and base-exchange (Table 1).

Species Specificity for Exchange/Acetyltransfer.

Comparisons of k$_{cat}$ (exchange) and the corresponding k$_{cat}$ (deacetylation) for each enzyme (Table 1) reveal that these parameters are enzyme specific. For the bacterial enzyme the measured value of k$_{cat}$ (exchange) is 5.1 times slower than k$_{cat}$ (deacetylation). In contrast, for the yeast and mouse enzymes, the values of k$_{cat}$ (exchange) exceed the values of k$_{cat}$ (deacetylation) by 3.5 and 11 fold respectively. The effi-

TABLE 1

Parameters for inhibition, exchange and deacetylation reactions for SIR2 enzymes

| Enzyme | k$_{cat}$ (deacetylation) min$^{-1}$ | k$_{cat}$ (exchange) min$^{-1}$ | k$_{inh}$ (deacetylation) min$^{-1}$ | K$_m$ (exchange) μM | K$_i$ (deacetylation) μM |
|---|---|---|---|---|---|
| Bacterial | 1.8 ± 0.2 | 0.35 ± 0.04 | 1.4 ± 0.2 | 37 ± 9 | 26 ± 4 |
| Yeast | 1.8 ± 0.2 | 5.8 ± 0.4 | 0.60 ± 0.08 | 160 ± 36 | 120 ± 25 |
| Mouse | 0.27 ± 0.03 | 3.0 ± 0.2 | 0.014 ± 0.002 | 127 ± 33 | 160 ± 50 |

$^a$Reactions are initial rate measurements under conditions that saturate the enzyme (600M NAD and 300M peptide substrate pH 7.8).
The respective parameters are measured in the following ways:
k$_{cat}$ (deacetylation) is the rate of deacetylation reaction for the enzyme in the absence of added nicotinamide.
k$_{cat}$ (exchange) is determined from the saturation curves for exchange shown in FIG. 1.
k$_{inh}$ (deacetylation) is the residual deacetylation rate in the presence of 2 mM nicotinamide.
The K$_m$ (exchange) values are determined from the fits of the Michaelis Menten equation to the plots in FIG. 1.
The K$_i$ (deacetylation) values are derived from curve fits shown in FIGS. 2 and 3.

Figure 3:
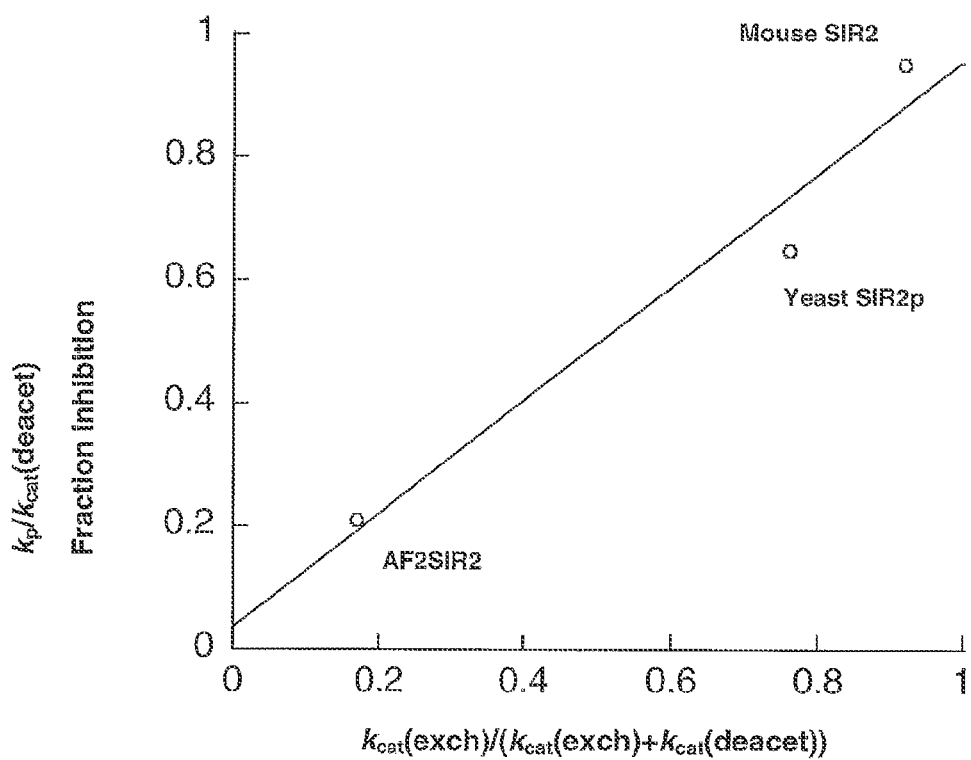
FIG. 3 shows a graph of the correlation of fractional inhibition and fraction exchange for the three enzymes at nicotinamide site saturation.

In the same experiments, ADPR and 3'-O-acetyl-ADPR products were measured to compare rates of deacetylation reactions relative to base-exchange reactions in the mixtures. The production of these compounds is stoichiometrically linked with lysine deacetylation and can be used to quantify deacetylation (Sauve et al., 2001; Jackson & Denu, 2002; Tanner et al., 2000; Tanny & Moazed, 2001). Deacetylation rates are expressed as a percentage of uninhibited rate and ciency of exchange versus deacetylation is a predictor of inhibition; thus, the bacterial enzyme is modestly inhibited by nicotinamide and the mouse enzyme is most inhibited (FIG. 2A-C). This relationship is summarized in a plot of the ratio k$_p$/k$_{cat}$ (deacetylation) versus k$_{cat}$ (exchange)/(k$_{cat}$ (deacetylation)+k$_{cat}$ (exchange)) for the three enzymes (FIG. 3). The near-linear relationship supports with the proposal that exchange and deacetylation compete for a common intermediate according to rate constants $k_4$ and $k_5$ respectively (Scheme 1). The rate of deacetylation is maximum without nicotinamide and its presence causes chemical reversal of the intermediate to the Michaelis complex.

Inhibiting the Base-Exchange Reaction.

The nicotinamide switch between deacetylation and exchange predicts that nicotinamide analogues inert as exchange substrates will not significantly inhibit deacetylation since they cannot chemically trap the ADPR-peptidyl intermediate (Scheme 1). The nicotinamide analogues of Table 2 did not inhibit SIR2 deacetylation for bacterial or yeast enzymes at 5 mM concentration, and only modest inhibition of the mouse enzyme was observed. None of the compounds tested were effective inhibitors of SIR2 base exchange for the yeast enzyme at saturating nicotinamide concentration (Table 2). Special conditions where yeast SIR2 deacetylation and base-exchange were performed in the presence of 35 M [carbonyl-$^{14}$C]nicotinamide and 42 mM isonicotinamide gave a 40% reduction in exchange rate with a corresponding 5% decline in deacetylation rate (Table 2).

Rate Constants or Intermediate Formation and Decomposition.

The rate constants $k_3$, $k_4$ and $k_5$ as defined in Scheme 1 for the mouse and yeast enzymes can be obtained with modest assumptions. For these enzymes $k_{cat}$(exchange)>$k_{cat}$(deacetylation) by at least a factor of 3. Since they share a common rate constant $k_3$ then $k_3$>$k_5$ and $k_4$>$k_5$ by at least a factor of 3. Therefore, we assume $k_5$=$k_{cat}$(deacetylation). The relation $k_4/k_5$=$k_{cat}$(exchange)/$k_{int}$ where $k_{int}$ is the residual deacetylation rate reflects the ratio of the two competing rates that deplete the ADPR intermediate. These ratios are 220, 9.8 and 0.25 for inhibition for the mouse, yeast and bacterial enzymes respectively. Calculation of $k_4$ using $k_5$ determines that $k_3$ is rate limiting for exchange for the mouse and yeast enzymes. Therefore, the final rate can be approximated $k_3$=$k_{inh}$+$k_{cat}$(exchange). These simple assumptions allow quantitation of the exchange rate $k_{cat}$(exchange), the deacetylation rate $k_{cat}$(deacetylation) and the residual rate $k_{inh}$ (Table 3). These assumptions predict that $K_m$ (exchange)=$K_i$ as is observed experimentally. The calculated rates assuming satu-

TABLE 2

Inhibition properties of nicotinamide analogues in SIR2 reactions.

| Compound | Inhibition of exchange rate (%)[a] | | Inhibition of deacetylation (%)[b] | |
|---|---|---|---|---|
| | yeast | bacterial | yeast | mouse |
| Thionicotinamide | ND | 4 | 15 | 16 |
| Pyrazinamide | ND | 4 | 1 | 1 |
| Benzamide | ND | 5 | 0 | 44 |
| Isonicotinamide | ND | 4 | 0 | 18 |
| Isonicotinamide[c] | 40 ± 5[c] (n = 6) | | 5 ± 5[c] (n = 6) | |

[a]Inhibition of nicotinamide base-exchange rate at 320 μM [carbonyl-$^{14}$C]nicotinamide and 5 mM of the given compound.
[b]Inhibition of deacetylation in the presence of 5 mM of given compound and no added nicotinamide. The errors of measurements do not exceed ±10%.
ND: No inhibition of exchange detected.
[c]Conditions: 0.5 μM yeast SIR2, 42 mM isonicotinamide, 35 μM [carbonyl-$^{14}$C]nicotinamide, 1 mM NAD$^+$, and 300 μM peptide, pH 7.6.
None of the compounds were base-exchange substrates.

rating conditions and equilibrium binding for peptide and NAD$^+$ agree to within 20% of the observed experimental values.

TABLE 3

Kinetic and thermodynamic parameters for SIR2 reactions.

$$\text{Substrates} \underset{k_4}{\overset{k_3}{\rightleftharpoons}} [\text{AMP-O-P(O)(O}^-)\text{-O-ribose-N}^+\text{-nicotinamide-CONH}_2 \cdots \text{acetyl-peptide intermediate}] \xrightarrow{k_5} \text{Products}$$

| Enzyme | $k_4/k_5$ | $k_3$ min$^{-1}$ | $k_4$ min$^{-1}$ | $k_5$ min$^{-1}$ | $K_{eq}$ ($k_3/k_4$) |
|---|---|---|---|---|---|
| Bacterial | 0.25 | >1.8 | 0.25 $k_5$ | >1.8 | ND |
| Yeast | 9.6 | 7.8 | 16.2 | 1.7 | 0.48 |
| Mouse | 220 | 3.0 | 59.4 | 0.27 | 0.055 |

The depicted rate constants and equilibrium parameters are defined according to the reaction. The parameters are calculated as follows:
The ratio $k_4/k_5$ is calculated by the ratio of $k_{cat}$ (exchange)/$k_{inh}$ (deacetylation) as defined in Table 1 and as explained in the text.
For the yeast and mouse enzymes the value of $k_3$ is determined by $k_{cat}$ (exchange)/$k_{inh}$ (deacetylation).
The value $k_5$ is determined from $k_{cat}$ (deacetylation).
The value of $k_4$ is computed from the rate constants $k_3$ and $k_4$.
Assumptions are justified in the text and give errors for calculation of steady state parameters by no more than 20%. Errors are determined from individual steady-state parameters in Table 1.
ND: Cannot be determined.

Discussion

SIR2 Biology.

SIR2 enzymes use the central metabolite NAD$^+$ to deacetylate proteins that are modified and regulated by acetyllysine groups. Targets that have been identified for the SIR2 proteins include H3 and H4 histone N-terminal tails (Landry et al., 2000a; Imai et al., 2000), p53 (Sauve et al., 2001; Vaziri et al., 2001; Luo et al., 2001), tubulin (North et al., 2003), bacterial acyl-CoA synthetase (Starai et al., 2003) and the bacterial DNA binding protein Alba (Bell et al., 2002). SIR2 enzymes are proposed to be sensitive to global metabolic states of the cell with activity adjusted accordingly. In principle, because the enzyme utilizes NAD$^+$ as a substrate, it can be regulated by changes in intracellular NAD$^+$ levels (Lin & Guarente, 2002; Campisi, 2000). Alternatively the NAD$^+$ metabolite nicotinamide can regulate SIR2 biochemical function in vivo. Recent biological studies in yeast support this view (Anderson et al., 2003; Bitterman et al., 2002; Anderson et al., 2002). Nicotinamide is a product of NAD$^+$ metabolism, a product in the SIR2 reaction, a base-exchange substrate (Landry et al., 2000b; Min et al., 2001; Sauve al., 2001) and an inhibitor of the SIR2 enzymatic reaction (Bitterman et al., 2002; Landry et al., 2000b). According to the mechanism of SIR2 catalysis in Scheme 1, base-exchange catalysis must cause inhibition of SIR2 deacetylation because exchange depletes the enzyme of the ADPR-intermediate that partitions between exchange and deacetylation reactions.

Nature of the Covalent Intermediate.

The ADPR-intermediate is formed by an ADP-ribosylation of the acyloxygen of the acetyllysine substrate and $^{18}$O studies have established that a C1'-O bond is formed between the acyl-oxygen and NAD$^+$ (Sauve et al., 2001). Although this intermediate is chemically unusual, it can form because the electrophilicity of an oxacarbenium ion transition state is sufficient to trap the weak nucleophile amide of the acetyl-peptide. Transition-state analysis of ADP-ribosyl transfer reactions suggest that weak nucleophilic participation at the transition state is a general feature of these reactions and that the ADP-ribosyl cation is indiscriminate for nucleophiles (Berti & Schramm, 1997; Scheuring & Schramm, 1997). In addition, glycosyl-amidates are reaction intermediates in glycosyltransferase reactions where they can form reversibly as reaction intermediates (Knapp et al., 1996; Zechel & Withers, 2000). The enzyme-bound intermediate has sufficient chemical reactivity to undergo reversal to reform NAD$^+$ in the presence of nicotinamide. This exchange reaction is general to all SIR2 enzymes that have been examined (Landry et al., 2000b; Min et al., 2001). The intermediate also activates the amide to form the eventual deacetylation products; 2'-O-acetyl-ADPR and the deacetylated lysine substrate (Sauve et al., 2001).

Single-Site Action of Nicotinamide.

Saturation by nicotinamide does not compete for binding with NAD$^+$ or peptide at the concentrations examined, consistent with a previous report (Bitterman et al., 2002). On the basis of the lack of nicotinamide inhibition of base-exchange reactions at 2 mM nicotinamide and the $K_m$ values for NAD$^+$ with the three enzymes (100-200 μM), the $K_i$ for competition between nicotinamide and NAD$^+$ is in excess of 8 mM. The inhibition of deacetylation by nicotinamide is entirely explained by the interaction of base with the covalent intermediate to reform NAD$^+$ and acetyl-protein. Although unusual, base reversal is precedented by the saturation kinetics for nicotinamide exchange for the ADP-ribosyl-transferase/cyclase enzyme CD38 (Sauve et al., 1998).

Species Dependent Inhibition by Nicotinamide.

Yeast and bacterial SIR2s show partial inhibition by nicotinamide even at >10 $K_i$ nicotinamide concentration (data not shown). Deacetylation rates were reduced by 21% and 65% but the mouse enzyme was inhibited 95% by nicotinamide with a $K_i$ value of 160 μM. A single site rapid-exchange binding model for nicotinamide that attenuates deacetylation and increases exchange is consistent with all experimental data. The observation that mouse SIR2 is most inhibited suggests that the mammalian enzymes may be subjected to strong regulation by nicotinamide.

Mechanism of Partial Versus Complete Nicotinamide Inhibition.

Partial inhibition can occur in the covalent SIR2 mechanism if the intermediate reacts forward to products even if the nicotinamide site is saturated. In the related nicotinamide exchange and cyclization reactions catalyzed by CD38, complete inhibition of cyclization occurs at nicotinamide saturation because the covalent ADPR-Glu intermediate cannot cyclize until nicotinamide departs the site (Sauve et al., 1998; Sauve et al., 2000). For CD38 the intermediate reacts only at the β-face and nicotinamide blocks access to other nucleophiles, while in the SIR2 intermediate both α and β-face reactions occur.

Chemical Partitioning of the SIR2 Intermediate.

Figure 5:
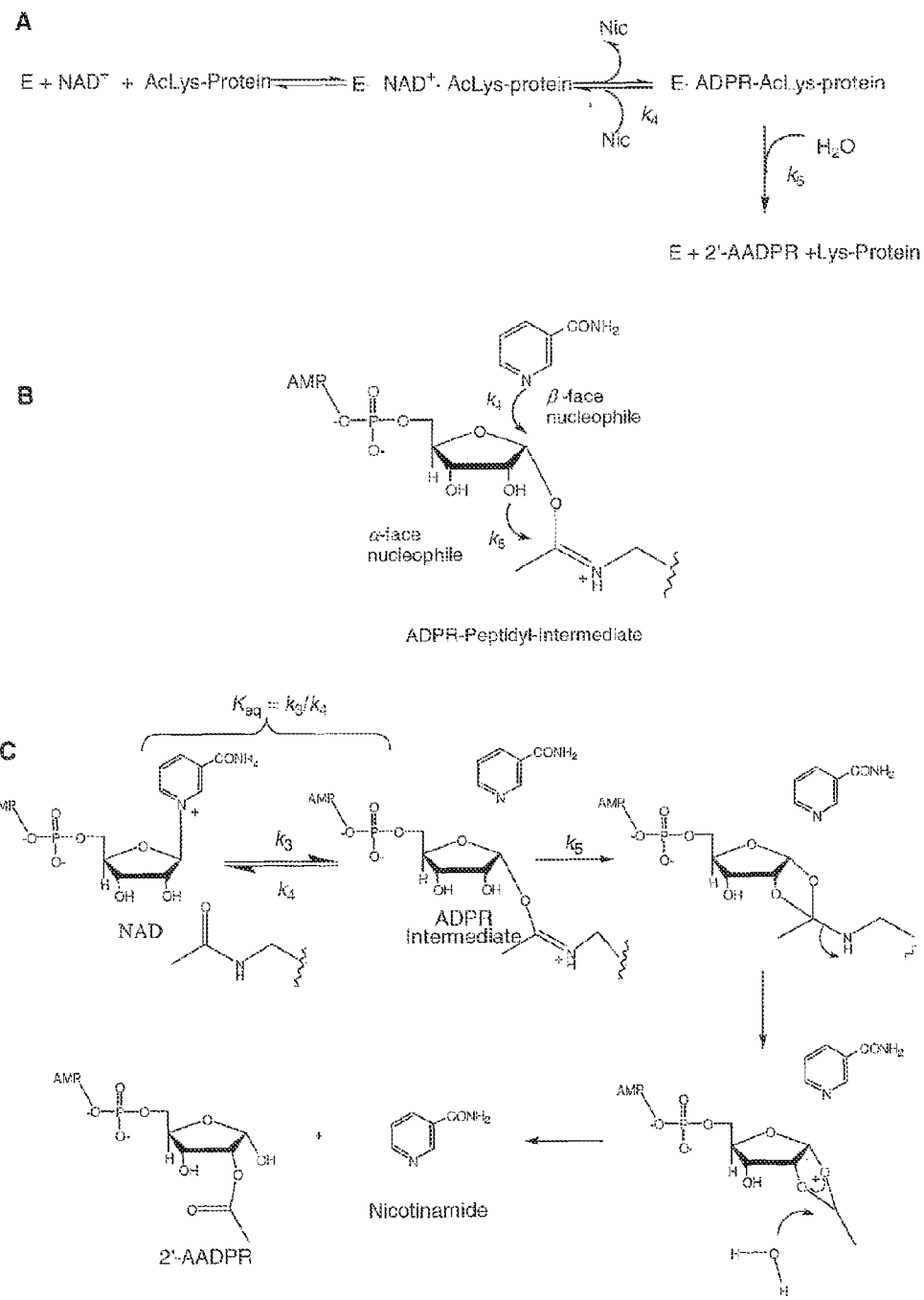
FIG. 5 shows Scheme I, which depicts aspects of the SIR2 reaction with acetylated peptides. Panel A is an abbreviated reaction scheme for SIR2 deacetylation reactions. Panel B is a diagram showing that competitive nucleophilic attacks on the SIR2ADPR-peptidyl intermediate occur from both stereochemical faces. The top face of the ribosyl ring is designated β, and nicotinamide nucleophilic attack at C1' leads to the re-formation of β-$NAD^+$. The bottom face of the sugar is designated Δ, and the hydroxyl group attacks the Δ-amidate group from the same face to generate deacetylation products. The rate constants for the two competing nucleophilic attacks are shown as $k_4$ for exchange and $k_5$ for deacetylation. Panel C shows reactions of SIR2 intermediates in saturating nicotinamide concentrations (binding steps are omitted).

The dual reactivity of the SIR2-ADPR intermediate is demonstrated by the ability of the enzyme to catalyze both base exchange and deacetylation chemistry from a common intermediate, even at saturating nicotinamide. The reactivity between exchange and deacetylation reactions occurs according to the rate constants $k_4$ (exchange) and $k_5$ (product formation) when nicotinamide is bound. This competition partitions the intermediate forward and backward to provide partial inhibition of deacetylation (FIG. 2A,B). The independence of the deacetylation and exchange reactions establishes that exchange is a β-face process, whereas deacetylation is an α face process (FIG. 5—Scheme 1B). $^{18}O$ studies have established that water does not attack at the β face at C1', but acts as a nucleophile at the α face, by attack of the acyl-carbonyl carbon (Scheme 1C; Sauve et al., 2001). In principle, these two stereofacially separated chemical processes can act in steric independence of each other, and can compete competitively to deplete intermediate on the enzyme.

Nicotinamide partition ratios are controlled by the relative rates of chemistry at the β versus the α face of the intermediate. A plot of fractional inhibition versus the ratio of $k_{cat}$(exchange)/$k_{cat}$(deacetylation) shows that nicotinamide inhibition is strongly correlated to the ratio (FIG. 3). The exchange and deacetylation reactions share the intermediate forming step $k_3$, and the ratio is determined by the chemical processes defined as $k_4$ for exchange and $k_5$ for deacetylation (Scheme 1C). Both $k_4$ and $k_5$ are slow, thus rapid intermediate reactivity is unlikely to be the cause of incomplete inhibition by nicotinamide. The rate of exchange from the intermediate is faster than deacetylation steps in yeast and mouse enzymes and are slow relative to typical enzyme binding steps. Thus, separate bifacial competition for the reactive intermediate is the likely mechanism of nicotinamide inhibition. A prediction of this model is that nicotinamide analogues inhibit SIR2 enzymes according to their base-exchange behavior. Nicotinamide analogs are poor inhibitors of deacetylation, and are not base-exchange substrates (Table 2). An exception is the mouse enzyme, where up to 45% reduction of deacetylation rate is observed. For the yeast enzyme these derivatives are also poor inhibitors of nicotinamide base exchange, suggesting poor binding to the intermediate or apo forms of the enzyme.

Changing the Deacetylation/Exchange Ratio.

As proof of concept for manipulation of the exchange/deacetylation ratio, low nicotinamide and increased isonicotinamide concentrations led to a 40% reduction in exchange versus control, but only a 5% reduction in deacetylation (Table 2). Thus, base-exchange can be inhibited preferentially over deacetylation. This result is consistent with the independence of chemical processes of the intermediate. Competitive binding of isonicotinamide and nicotinamide results in a decline in base-exchange (β-face chemistry) with little effect on deacetylation (α-face chemistry).

Reaction Coordinate Diagrams for SIR2s.

Figure 4:
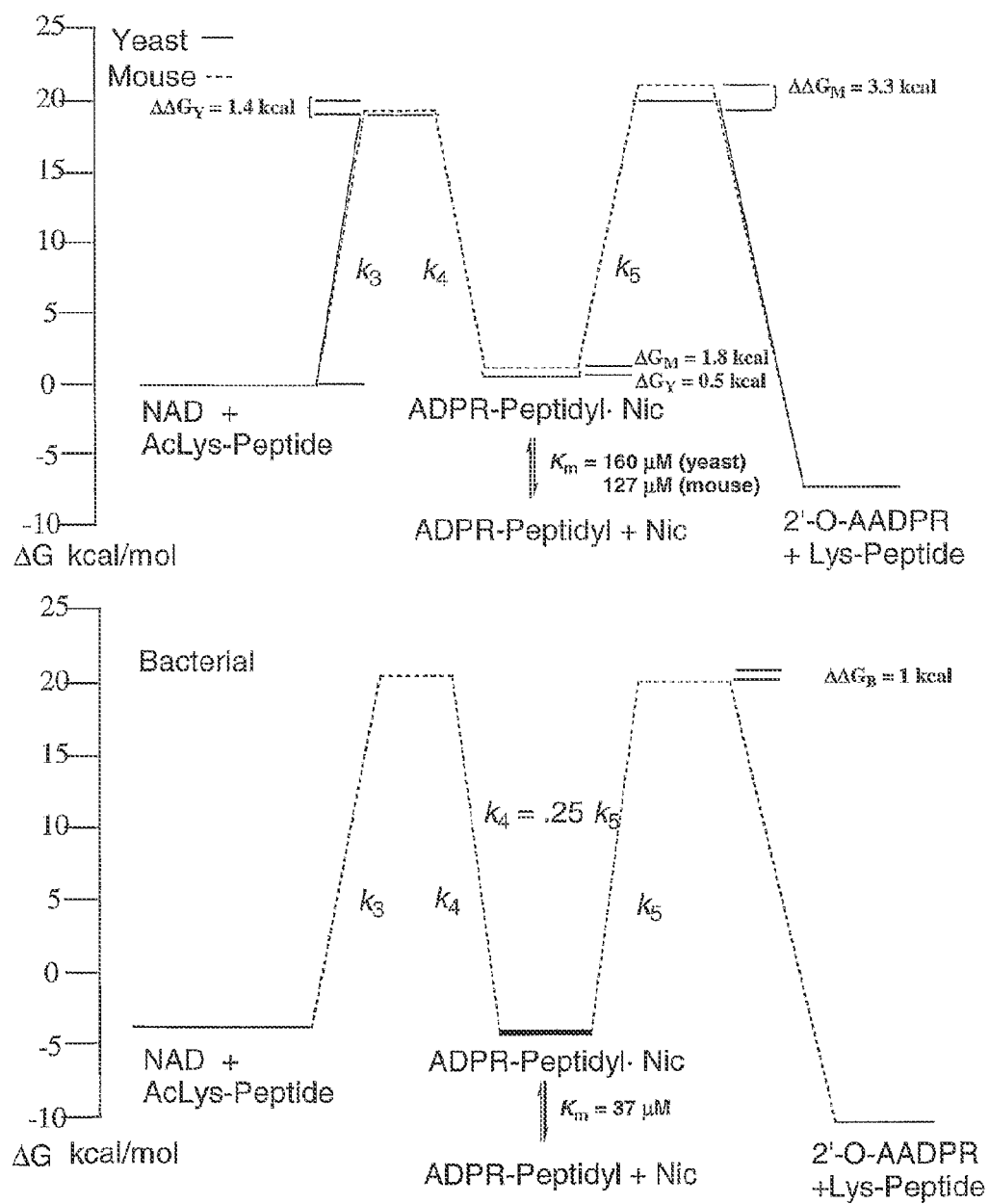
FIG. 4 shows graphs of reaction coordinates for SIR2 reactions based on values of $k_3$, $k_4$, and $k_5$ of the bacterial, yeast and mouse enzymes (Table 3). For the bacterial enzyme only relative barrier heights are known and the relative energy of the intermediate is undetermined. Binding events are not shown. $\Delta G_M = \Delta G_M$ (intermediate)$-\Delta G_M$(Michaelis); $\Delta G_Y = \Delta G_Y$ (intermediate)$-\Delta G_Y$ (Michaelis); $\Delta\Delta G_M = \Delta G_M$ (hill 2)$-\Delta G_M$ (hill 1); $\Delta\Delta G_Y = \Delta G_Y$ (hill 2)$-\Delta G_Y$ (hill 1); $\Delta\Delta G_B = \Delta G_B$ (hill 1)$-\Delta G_B$ (hill 2).

Reaction coordinate diagrams illustrate the energetic model of SIR2 catalysis and inhibition (FIG. 4). The reaction coordinates for the mouse and yeast enzymes show that the ADPR-intermediate is isolated by large energy barriers that account for the slow catalytic rates characteristic of the SIR2 enzymes. These barriers demonstrate the stable intermediate and the equilibration of binding steps of substrates and products. In the case of bacteria the energy of the intermediate could not be established. Poor inhibition by nicotinamide may be barrier height modulation, an equilibrium effect in the first intermediate or both. Raising the energy of the intermediate increases sensitivity of the enzyme intermediate to reversal by nicotinamide if the rate of deacetylation remains unchanged. The differences in the ability of nicotinamide to inhibit the mouse and yeast enzymes are due to the barriers between the ADPR intermediate, the Michaelis complex and products. For the mouse enzyme, the equilibrium constant is in favor of the Michaelis complex and inhibition by nicotinamide was >95% (Table 3). For the yeast enzyme this equilibrium value is 0.48 and the inhibition by millimolar nicotinamide was 65% of the uninhibited rate. When nicotinamide concentrations are low, destabilization of the intermediate would not compromise catalytic efficiency, since the intermediate is trapped by nicotinamide dissociation from the enzyme.

Conclusions.

The mechanism of SIR2 catalysis presented here interprets the inhibition of nicotinamide to be a consequence of its chemical attack of a peptidyl-ADPR intermediate. The data can be analyzed completely with the proposed reaction mechanism for SIR2 base exchange and deacetylation (Sauve et al., 2001). The findings suggest a chemical means for increasing the cellular activity of SIR2. Nicotinamide degradation has been suggested as a way to release SIR2 from inhibition (Anderson et al., 2003). Alternatively, nicotinamide analogues capable of inhibiting base-exchange but not deacetylation would cause in vivo activation of SIR2 and is currently under investigation.

Methods and Materials

Yeast SIR2p was expressed from a plasmid generously provided by the Guarente laboratory (Imai et al., 2000). Bacterial SIR2Af2 was expressed from a plasmid generously provided by the Wolberger laboratory (Smith et al., 2000). Mouse SIR2 enzyme was obtained from Upstate Group in purified form. Reverse phase HPLC were performed on a Waters Delta 600 pump, 717 autosampler, and a dual wavelength 2486 detector. The p53 peptide was obtained from commercial sources.

SIR2 Exchange and Deacetylation Assays.

Reaction mixtures of 50 μL of 50 mM potassium phosphate pH 7.8 containing 300 μM KKGQSTSRHK(KAc)LMFK-TEG peptide and 600 M $NAD^+$ containing selected concentrations of [carbonyl-$^{14}C$]nicotinamide 60 μCi/mol (0, 10, 20, 30, 45, 60, 80, 90, 125, 250, 360, 600, 1200) were reacted with 1 μM SIR2 enzyme added as a 1 μL addition of concentrated enzyme. After 2 hours, aliquots of 10 μL removed at 0, 30, 60, 90 and 120 min. Each aliquot was combined with 50 μL 50 mM ammonium acetate pH 5.0 to quench and assayed by HPLC for deacetylation products and $NAD^+$. The chromatograms (260 nm) were obtained using 50 mM ammonium acetate pH 5.0 as eluant on a semi-preparative Waters C-18 column (2.0 mL/min flow rate). Peaks for ADPR and 3'-O-Acetyl-ADPR were quantified by integration. The peak for NAD+ was collected and radiation counted. Plots of rate versus nicotinamide concentration were fit using the curve $v=k_{cat}[S]/([S]+K_m)$ with the curve-fitting feature of Kaleidagraph. Plots of deacetylation rate versus nicotinamide were fit to the equations described in the text. Experiments with 2 mM nicotinamide established the effects of this concentration on the deacetylation and exchange activity of the SIR2 enzyme.

Inhibition of Deacetylation with Nicotinamide Isosteres.

Reactions were as above but base reactions contained 5 mM of pyrazinamide, isonicotinamide, thionicotinamide, or benzamide. Reactions were carried out (2 hours for AF2 and yeast enzymes and 3 hours for mouse enzyme) at 37° C. and quenched by addition of 80 µL 50 mM ammonium acetate pH 5.0. Product formation was quantified by HPLC. Thionicotinamide-NAD+ was synthesized by CD38. Rates were compared with controls lacking added base.

Example 2

Chemical Activation of Sir2-Dependent Transcriptional Silencing by Relief of Nicotinamide Inhibition Example Summary In vivo activation of enzymatic activity by small molecule effectors is rare. The unusual mechanistic (Imai et al., 2000; Landry et al., 2000a; Smith et al., 2000; Sauve et al., 2001) and regulatory (Lin et al., 2000; Kaeberlein et al., 2002; Anderson et al., 2002; Sandmeier et al., 2002; Bitterman et al., 2002; Anderson et al., 2003; Lin et al., 2004; Lin et al., 2003) features of Sir2 suggests a small molecule approach to achieve in vivo activation of transcriptional silencing (Rusche et al., 2003). NAD+ dependent protein deacetylation by Sir2 involves an ADP-ribosyl-imidate intermediate (Sauve et al., 2001). Nicotinamide inhibits Sir2 deacetylase activity by chemical depletion of this intermediate (Sauve and Schramm, 2003; Jackson et al., 2003), however, the importance of nicotinamide inhibition of Sir2 in vivo is debated (Anderson et al. 2003; Lin et al., 2004; Lin et al., 2003). We demonstrate that nicotinamide inhibition of Sir2 catalytic activity is antagonized in vitro by isonicotinamide and leads to an increase in Sir2 deacetylation activity. Moreover, isonicotinamide substantially increases transcriptional silencing at Sir2-regulated genetic loci. These studies demonstrate that a small molecule agonist can relieve nicotinamide inhibition of Sir2 and provide chemical-biological evidence that nicotinamide is an endogenous regulator of Sir2, Results and Discussion Yeast Sir2 is a class III histone deacetylase that uses NAD+ to deacetylate acetyllysine residues at the N-terminal tails of histones H3 and H4 in chromatin (Imai et al., 2000; Landry et al., 2000a; Smith et al., 2000). Sir2 function is necessary for the formation and spreading of heterochromatin and for transcriptional silencing at the silent mating type loci, at telomeres and in the rDNA repeat (Rusche at al., 2003). Elevated SIR2 gene dosage increases transcriptional silencing and genome stability and leads to extension of yeast replicative lifespan (Kaeberlein et al., 1999). Calorie restriction and high osmolarity also increase yeast lifespan through Sir2-dependent pathways (Lin et al., 2000; Kaeberlein et al., 2002). These stimuli upregulate Sir2 catalytic activity without increasing the level of Sir2 protein (Anderson et al., 2002). However the mechanism of upregulation and the endogenous regulator(s) of Sir2 activity remain controversial. Nicotinamide (Bitterman et al., 2002; Anderson et at, 2003), NADH (Lin et at, 2004) and NAD+ (Imai et al., 2000; Landry et al., 2000a; Smith et al., 2000; Lin et al., 2000) have each been proposed as the principal regulator of Sir2 catalysis in vivo. Cellular stress is believed to lower the concentrations of inhibitory Sir2 regulators (Anderson et al., 2003; Lin at al., 2004; Lin et al., 2003). Since calorie restriction increases lifespan in organisms from yeast to primates and sirtuins affect lifespan and cell survival in multicellular eukaryotes (Tissenbaum and Guarente, 2000; Vaziri at al., 2001; Luo et at, 2001), the question of Sir2 regulation is currently at the forefront of Sir2 biology (Hekimi and Guarente, 2003). Understanding Sir2 regulation based upon nicotinamide inhibition can be used to develop strategies for chemical control of Sir2 activity that provide direct modulation of sirtuin function independent of genetic methods.

Sir2 deacetylation chemistry yields nicotinamide, the lysine amino group and the unusual metabolite 2'-O-acetylADPR (Sauve et al., 2001) (FIG. 6a). The catalytic mechanism is initiated by formation of a long-lived peptidyl-imidate intermediate. Nicotinamide achieves binding equilibrium with the imidate-enzyme complex and can react to regenerate acetyllysine and NAD (Sauve and Schramm, 2003; Jackson et al., 2003) in a so-called base-exchange reaction (FIG. 6a, $k_4$). This reaction depletes the imidate intermediate during normal steady state turnover causing nicotinamide inhibition of deacetylation (Sauve and Schramm, 2003; Jackson et al., 2003). These findings are consistent with the proposal that changes in nicotinamide concentration in vivo can regulate Sir2 function (Anderson et al., 2003; Gallo et al., 2004). Incomplete Sir2 inhibition by nicotinamide supports a mechanism where nicotinamide and the 2'-hydroxyl of the ribose ring react independently with the peptidyl-imidate (FIG. 7b) (Sauve and Schramm, 2003). Deacetylation of an N-terminal histone H4 peptide is inhibited by nicotinamide ($K_i$=100 µM) and declines asymptotically to 19% of the uninhibited rate. This limit establishes the partitioning of the imidate-enzyme complex between base exchange and deacetylation reactions and is described by the ratio of rate constants $k_4$ and $k_5$ (FIG. 1a) (Sauve and Schramm, 2003). Thus, the chemical mechanism of Sir2 predicts that a non-reactive nicotinamide isostere bound in the nicotinamide site could selectively prevent base exchange and thereby increase deacetylation rates (FIG. 6b) (Sauve and Schramm, 2003).

To evaluate this prediction we determined the effect of isonicotinamide on base exchange and deacetylation rates. Isonicotinamide increased the apparent $K_m$ value for base exchange without significantly affecting $V_{max}$ (FIG. 7a), consistent with a specific competitive effect on nicotinamide binding and a non-competitive effect on NAD+ and peptide binding (FIG. 6c). The $K_i$ for isonicotinamide is 60 mM based on these curves. Isonicotinamide concentrations to 100 mM inhibit base exchange but do not substantially affect rates of deacetylation in the absence of nicotinamide (FIG. 7b). Nicotinamide inhibits deacetylation (FIG. 7b) with good agreement between $K_i$ (deacetylation) and $K_m$ (exchange) at 0 mM isonicotinamide (Sauve and Schramm, 2003). Since isonicotinamide does not inhibit deacetylation but competitively inhibits base exchange, isonicotinamide is predicted to antagonize nicotinamide's inhibition of deacetylation. Accordingly, the $K_i$ (deacetylation) values for nicotinamide increased with the isonicotinamide concentration (FIG. 7b). Thus, isonicotinamide directly antagonizes nicotinamide inhibition of deacetylation by competitive inhibition with nicotinamide in the base-exchange reaction.

Physiological nicotinamide concentrations have been estimated to be 50-400 µM (Andersen et al., 2003). Levels as low as 100 µM are predicted to inhibit Sir2 catalysis independent of NAD+ concentrations in cells (Bitterman et al., 2002;

Anderson et al., 2003). We examined the effect of isonicotinamide concentrations on base-exchange and deacetylation activity in the presence of 125 µM [carbonyl-$^{14}$C]nicotinamide. Base exchange is inhibited by increasing isonicotinamide concentrations. Conversely, deacetylation activity is increased by as much as 45% over the same isonicotinamide concentration range (FIG. 7c). The inhibition of base exchange and the activation of deacetylation under these conditions suggests that functional control of Sir2 by nicotinamide can be relieved by isonicotinamide binding to the imidate-enzyme intermediate (FIG. 1).

Figure 6:
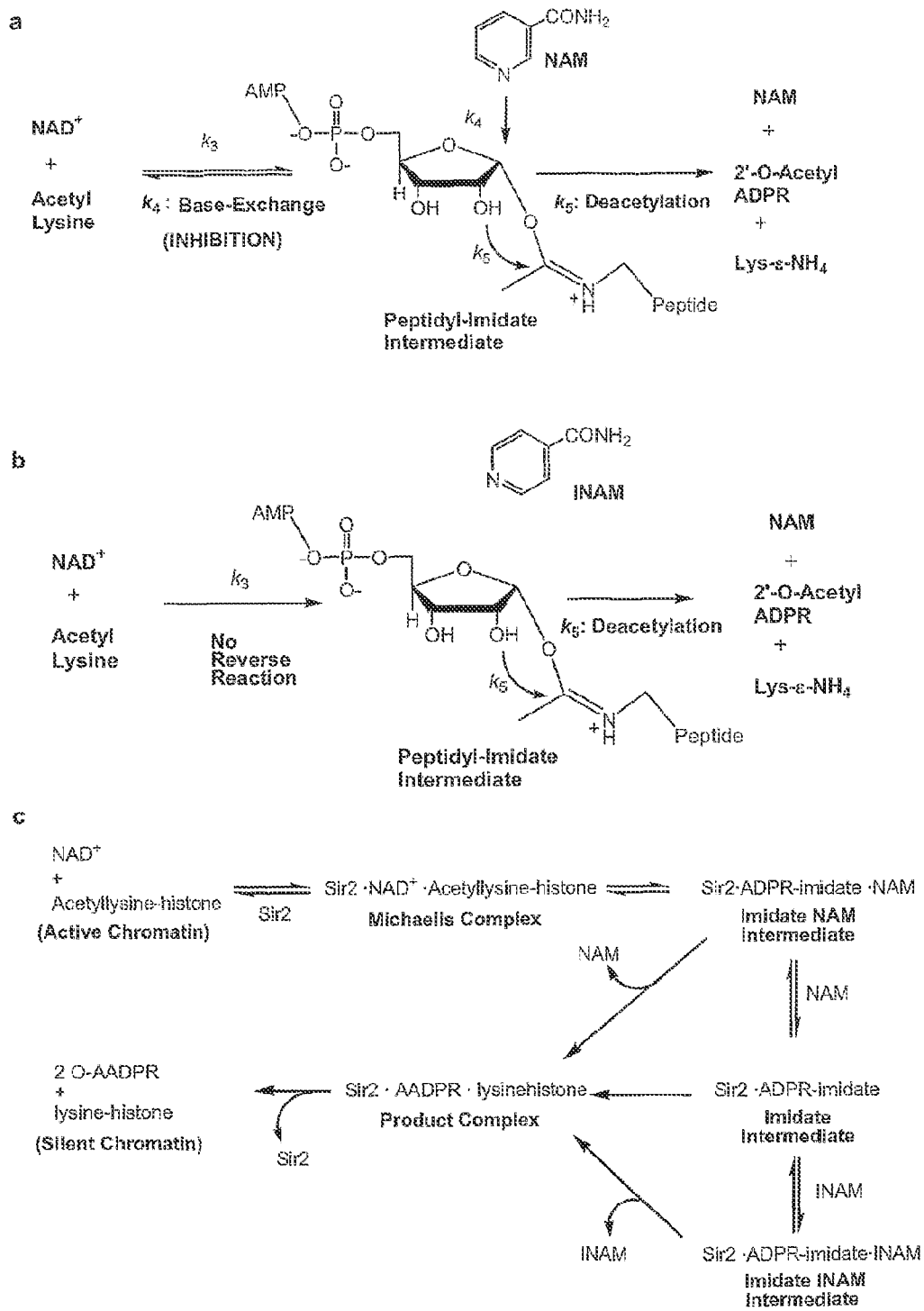
FIG. 6 shows schematic representations of ADP-ribosylimidate reactivity in Sir2-catalyzed base exchange and deacetylation reactions. As shown in Panel a, nicotinamide (NAM) and 2'-hydroxyl attacks occur on opposite faces of the ribose moiety leading to chemical competition between base exchange and deacetylation. Nicotinamide inhibition of deacetylation results from chemical reversal of the imidate intermediate. Panel b shows the proposed action of isonicotinamide (INAM) as a ligand at the nicotinamide binding site. Base exchange is not possible since the nitrogen atom is in an unreactive position. Efficient deacetylation occurs due to the chemical independence of the deacetylation and base-exchange reactions. Panel c shows a scheme for reaction of acetylated histone (active chromatin) with NAD+ and Sir2 inside yeast cells in the presence of isonicotinamide. Endogenous nicotinamide levels compete for ADPR-imidate with the exogenous ligand. The INAM complex cannot react to reform substrates. INAM does not inhibit reaction to form deacetylated histones (silent chromatin) and 2'-AADPR.
Figure 7:
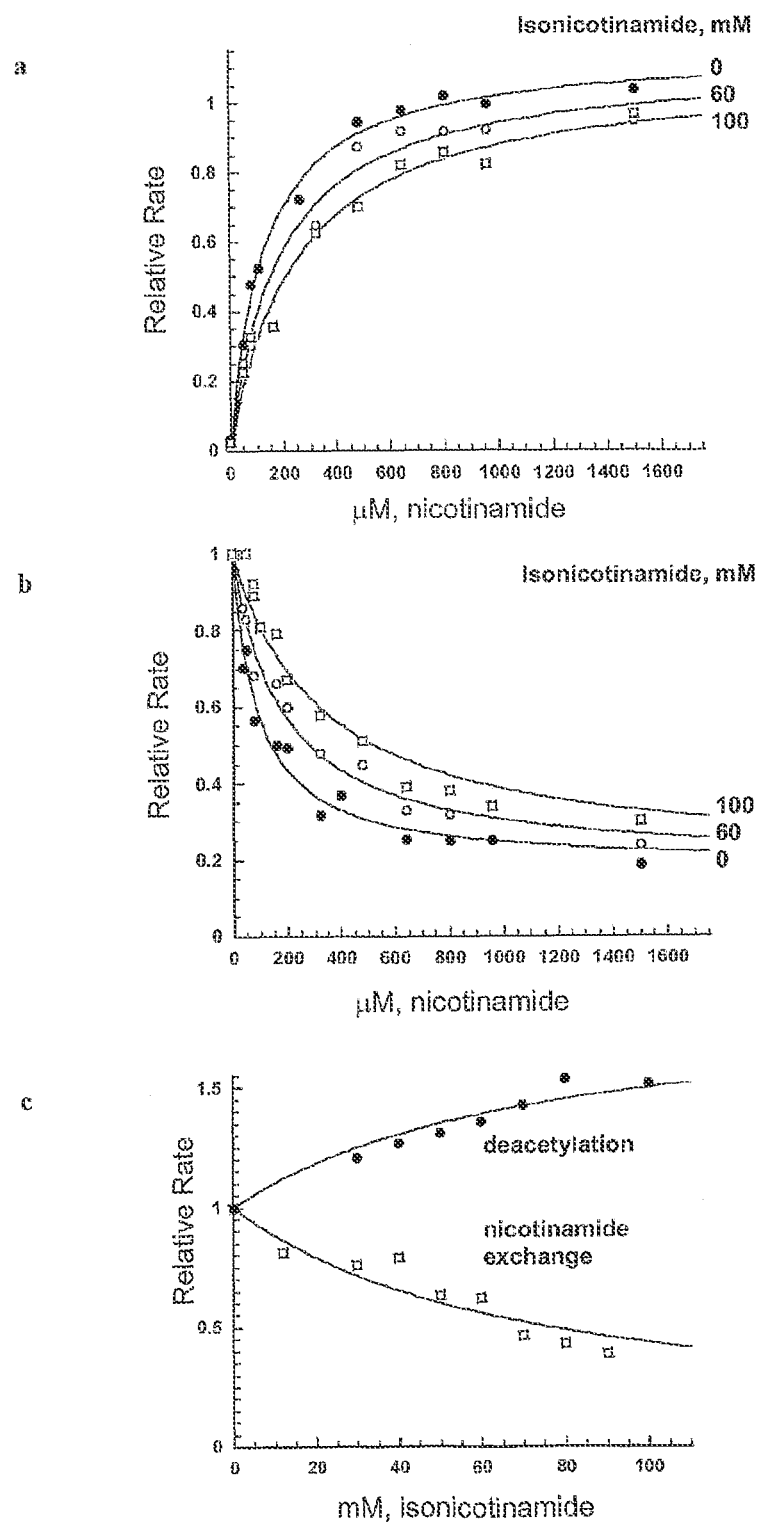
FIG. 7 is graphs showing experimental measurements of the Sir2 catalyzed exchange rate and deacetylation rate of the H4 N-terminal peptide, measured as a function of [carbonyl-

Isonicotinamide is expected to increase gene silencing at Sir2-regulated loci if the normal endogenous level of nicotinamide inhibits Sir2 function in vivo (FIG. 6c). We examined the effect of isonicotinamide on the expression of reporter genes integrated at each of the chromosomal loci that are subject to Sir2-dependent transcriptional silencing. Silencing of a telomeric URA3 gene (TEL-VIIL-URA3) confers resistance to 5-fluoroorotic acid (5-FOA). Isonicotinamide increased silencing of the telomeric URA3 gene, as indicated by the ~10-fold increase in colony growth on FOA-containing medium (FIG. 8a). Notably, isonicotinamide had no effect on colony survival on non-selective medium. In agreement with the competitive binding mechanism (FIG. 6), addition of isonicotinamide to nicotinamide-containing medium, which inhibits silencing (Bitterman et al., 2002), generated an intermediate growth phenotype (FIG. 8a). The enhanced silencing effect of isonicotinamide on this telomeric reporter gene was especially pronounced (>10$^3$ fold) in a dot1Δ strain, which is defective in histone H3-lysine 79 methylation. In this strain, silencing is reduced by dispersion of the Sir proteins from the telomeres (van Leeuwen et al., 2002). Thus, enhanced telomeric silencing caused by isonicotinamide in the dot1Δ strain serves to demonstrate the Sir2 specificity of the effect. Silencing of a second telomeric marker in these strains (ADE2 integrated at TEL-VR) was also increased by isonicotinamide (data not shown).

The effect of isonicotinamide on Sir2 activity at the silent mating-type loci was measured in an HMR: TRP1 strain by growth on medium lacking tryptophan (FIG. 8b). Silencing of TRP1 decreases growth on Trp$^-$ media. Consistent with the ability of isonicotinamide to increase the activity of Sir2, growth on Trp$^-$ medium was reduced significantly (10$^3$-40$^4$ fold) compared to medium lacking the compound. Conversely, the decrease in silencing caused by nicotinamide resulted in increased growth on Trp$^-$ medium. Neither compound altered the growth phenotype of an isogenic sir2Δ strain. Thus, as demonstrated at telomeric loci (FIG. 8a), the effects of nicotinamide and isonicotinamide are specific for Sir2 under these assay conditions. Isonicotinamide also increased Sir2 activity at HML (measured using HML:: URA3 strains, UCC3515 and UCC4574 (Singer et al., 1998), on FOA-containing medium; data not shown).

Sir2 also localizes to the nucleolus where it functions to propagate a specialized chromatin structure on the rDNA (Rusche at al., 2003). The silencing of RNA pol II-transcribed genes inserted into the rDNA array is sensitive to SIR2 gene dosage (Smith et al., 1998; Fritze et al., 1997) and is decreased by nicotinamide (Bitterman et al., 2002; Anderson et al., 2003; Gallo et al., 2004). The resistance of an RDN1:: URA3 strain to FOA, indicates that isonicotinamide increases silencing at the rDNA locus (FIG. 8c). Thus, isonicotinamide increases the activity of Sir2 in vivo at all three types of silent loci. Moreover, for the telomeric and HM loci, the effect of isonicotinamide was demonstrated using multiple reporter genes in both positive and negative selection assays.

Increased expression of the nicotinamidase encoded by PNC1 has been observed in response to a variety of stress conditions (see Smith et al., 1998) and is proposed to occur in calorie-restricted cells (Anderson et al., 2003). Overexpression of PNC1 can enhance Sir2-dependent silencing, extend lifespan and suppress the inhibitory effect of exogenous nicotinamide on these processes (Anderson et al., 2003; Gallo et al., 2004). To address whether enhanced silencing by isonicotinamide arose from induction of PNC1 rather a direct effect on Sir2 (FIG. 6b), we examined the effect of isonicotinamide in a pnc1Δ strain. Consistent with other studies (Sandmeier et al., 2002; Gallo et al., 2004), deletion of PNC1 generates a silencing defect at a telomeric URA3 gene (TEL-VR-URA3, FIG. 9). This defect was readily reversed by the addition of isonicotinamide, as indicated by the pronounced (>10$^4$ fold) increase in colony growth on FOA-containing medium (FIG. 9). Similarly, silencing at the HMR locus (HMR::TRP1) in the pnc1Δ strain was strongly enhanced by isonicotinamide and produced a dramatic (10$^3$ fold) reduction in growth on Trp$-$ medium (FIG. 9). As expected, these data demonstrate that isonicotinamide activation of Sir2 activity in vivo is independent of Pnc1.

In the NAD$^+$ salvage pathway, deamidation nicotinamide by Pnc1 produces nicotinic acid, which is converted into the corresponding mononucleotide by the product of the NPT1 gene. Deletion of NPT1 lowers the intracellular NAD$^+$ concentration two to three fold, weakens transcriptional silencing and abolishes lifespan extension by calorie restriction (Smith et al., 2000; Sandmeier et al., 2002; Lin et al., 2004). Nonetheless, isonicotinamide enhances the expression of a telomeric reporter gene in an npt1Δ strain (FIG. 9). Thus, isonicotinamide activation of Sir2 is not dependent on Npt1 and occurs despite decreased NAD$^+$ levels. The ability of isonicotinamide to enhance transcriptional silencing in the presence and the absence of key NAD$^+$ salvage enzymes (FIGS. 8 and 9), together with the mechanistic knowledge of its action in antagonizing nicotinamide base exchange (FIGS. 6 and 7), provides compelling evidence for nicotinamide as an endogenous effector of Sir2 deacetylase activity under normal cellular conditions.

The unusual mechanism of Sir2-catalyzed deacetylation permits unique opportunities for chemical intervention to enhance its enzymatic activity. Polyphenolic compounds have been proposed to increase Sir2 deacetylation activity by changes in the Michaelis constant for both the acetylated substrate and NAD$^+$ (Howitz et al., 2003). In contrast, nicotinamide inhibition and isonicotinamide activation of Sir2 deacetylase activity is achieved without affecting substrate or NAD$^+$ binding by altering the proportion of the imidate-enzyme complexes proceeding towards the deacetylated product (FIGS. 6c and 7) (Sauve and Schramm, 2003). These findings suggest that combinations of mechanistically distinct small molecule activators of Sir2 may further enhance deacetylase activity in vivo. Finally, we note that isonicotinamide and mechanistically similar Sir2 activators could be especially effective agonists of mammalian sirtuins, which are more potently inhibited by nicotinamide than the yeast Sir2 enzyme (Sauve and Schramm, 2003).

Example 3

2-Fluoronicotinamide Increases Sir2 Deacetylation by Inhibiting Base Exchange

Synthesis of 2-Fluoronicotinamide was achieved from commercially available 2-fluoro-3-methyl-pyridine by a route identical to a reported method (Minor et al., 1949). Briefly, the fluoromethylpyridine was heated in the presence of 6 oxidizing equivalents of potassium permanganate and the resulting fluoronicotinic acid isolated by filtration. Subsequent preparation of the acid chloride and treatment with ammonia gave the desired compound in good yield. This material was confirmed in structure by an NMR spectrum and a UV/vis spectrum. Purity was confirmed by reversed phase HPLC.

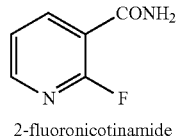

2-fluoronicotinamide

Use of this compound as a selective inhibitor of base-exchange reactions and not deacetylation reactions catalyzed by Sir2 enzymes derived from yeast and archaea is described. As previously noted the ability of a compound to behave as an activator of Sir2 catalysis in vivo depends upon its ability to relieve nicotinamide inhibition of Sir2 catalysis. Work featured in this patent shows that nicotinamide inhibition occurs via chemical depletion of an intermediate responsible for both base exchange and deacetylation chemistry. Therefore, an assay that simultaneously monitors both deacetylation and base exchange activity was used to assay for selective inhibition by small molecules conceived as possible activators.

We chose the preferred HPLC assay in which 35 µM [carbonyl-$^{14}$C]nicotinamide was incubated with 1 µg Sir2 enzyme, 300 µM histone H4 substrate and 600 µM. NAD$^+$ in 50 µL 50 mM potassium phosphate pH 7.0. Each solution also contained a variable amount of 2-Fluoronicotinamide with concentrations of 0, 5, 10, 20, 40 and 80 mM of the compound. After incubation of reactants for 30 minutes the reaction was quenched by addition of 200 mL 50 mM ammonium acetate pH 5.0, and then the full 250 µL solution injected onto a C-18 semipreparative column for separation of all NAD derived or nicotinamide derived compounds. Deacetylation was assayed by integration of the peaks for AADPR and ADPR in reaction mixtures. Base exchange reactions were assayed by collection of the nicotinamide and NAD peaks separately followed by scintillation counting of the fractions to quantitate recovered radioactivity. To ensure initial rate conditions the NAD radioactivity was no more than 10% of the total radioactivity in the nicotinamide peak. Table 4 shows the results.

TABLE 4

| Conc   | Cpm/sample | % rate | Area (DAP)   | % rate |
|--------|------------|--------|--------------|--------|
| Archaea enzyme ||||| 
| 0 mM   | 20,100     | 100%   | $4.0\ 10^5$  | 100%   |
| 5 mM   | 18,200     | 91%    | $4.0\ 10^5$  | 100%   |
| 10 mM  | 16,100     | 80%    | $4.0\ 10^5$  | 100%   |
| 20 mM  | 14,600     | 73%    | $4.0\ 10^5$  | 100%   |
| 40 mM  | 10,300     | 50%    | $4.0\ 10^5$  | 100%   |
| 80 mM  | 7,000      | 35%    | $4.0\ 10^5$  | 100%   |
| Yeast enzyme |||||
| 0 mM   | 32,300     | 100%   | $8.0\ 10^4$  | 100%   |
| 5 mM   | 24,500     | 76%    | $8.0\ 10^4$  | 100%   |
| 10 mM  | 18,800     | 58%    | $7.8\ 10^4$  | 97%    |
| 20 mM  | 15,200     | 47%    | $8.0\ 10^4$  | 100%   |
| 40 mM  | 11,600     | 36%    | $7.7\ 10^4$  | 95%    |
| 80 mM  | 9,000      | 28%    | $7.7\ 10^4$  | 95%    |

DAP: Deacetylation products.
Cpm/sample is amount of radioactivity in NAD peak.

From the inhibition curves of base exchange and the corresponding values of rates determined for deacetylation we confirmed that 2-fluoronicotinamide selectively inhibits only base exchange and not deacetylation as proposed for a biological activator of Sir2. These data also confirm that attenuation of the reactivity of the nicotinamide ring nitrogen by introduction of a fluoro-substitution to the nicotinamide ring causes displacement of the natural inhibitory ligand nicotinamide without the compound behaving like nicotinamide to inhibit deacetylation. This property of fluoronicotinamide is consistent with the chemical nature of Sir2 inhibition by nicotinamide. Therefore, it is clear from this study that activators may include small molecules resembling nicotinamide that can prevent nicotinamide binding because of diminished chemical reactivity with the covalent intermediate responsible for base exchange catalysis.

In view of the above, it will be seen that the several advantages of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

What is claimed is:

1. A composition formulated for topical administration comprising isonicotinamide in an amount effective to increase protein deacetylation by a SIR2 enzyme in a living cell.

2. The composition of claim 1, wherein the cell is an archaeal cell or a prokaryotic cell.

3. The composition of claim 1, wherein the cell is part of a living organism.

4. The composition of claim 1, wherein the cell is a human cell.

5. The composition of claim 3, wherein the living organism is a mammal.

6. The composition of claim 3, wherein the living organism is a human.

7. The composition of claim 1, wherein the SIR2 enzyme is selected from the group consisting of SIR2A, SIRT3, SIRT2p, SIRT1p, SIRT1, SIRT2, SIRT3, SIRT4, SIRT5, SIRT6 and SIRT7.

8. The composition of claim 1, wherein the composition includes one or more of propylene glycol, polyethylene glycol, isopropanol, ethanol, oleic acid, N-methylpyrrolidone, ethylcellulose, hydroxypropyl cellulose, ethylene/vinylacetate and polyvinyl pyrrolidone.

9. A composition formulated for topical administration comprising isonicotinamide in an amount effective to activate a SIR2 enzyme in a living cell.

10. The composition of claim 9, wherein the cell is in a mammal.

11. The composition of claim 9, wherein the cell is in a human.

12. The composition of claim 9, wherein the SIR2 enzyme is selected from the group consisting of SIR2A, SIRT3, SIRT2p, SIRT1p, SIRT1, SIRT2, SIRT3, SIRT4, SIRT5, SIRT6 and SIRT7.

13. The composition of claim 9, wherein the composition includes one or more of propylene glycol, polyethylene glycol, isopropanol, ethanol, oleic acid, N-methylpyrrolidone, ethylcellulose, hydroxypropyl cellulose, ethylene/vinylacetate and polyvinyl pyrrolidone.

* * * * *